US009956049B2

(12) United States Patent
Shmarak et al.

(10) Patent No.: US 9,956,049 B2
(45) Date of Patent: *May 1, 2018

(54) METHOD AND APPARATUS FOR INVASIVE DEVICE TRACKING USING ORGAN TIMING SIGNAL GENERATED FROM MPS SENSORS

(71) Applicant: MediGuide Ltd., Haifa (IL)

(72) Inventors: Itzhak Shmarak, Haifa (IL); Gera Strommer, Haifa (IL); Uzi Eichler, Haifa (IL)

(73) Assignee: MediGuide Ltd., Haifa (IL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/428,497

(22) Filed: Feb. 9, 2017

(65) Prior Publication Data
US 2017/0151023 A1    Jun. 1, 2017

Related U.S. Application Data

(63) Continuation of application No. 10/986,567, filed on Nov. 10, 2004, now Pat. No. 9,572,519, which is a
(Continued)

(51) Int. Cl.
*A61B 34/20* (2016.01)
*A61B 5/11* (2006.01)
(Continued)

(52) U.S. Cl.
CPC .............. *A61B 34/20* (2016.02); *A61B 5/066* (2013.01); *A61B 5/1102* (2013.01); *A61B 5/113* (2013.01);
(Continued)

(58) Field of Classification Search
CPC ......... A61B 34/20; A61B 34/10; A61B 5/066; A61B 5/1102; A61B 5/1107;
(Continued)

(56) References Cited

U.S. PATENT DOCUMENTS 3,937,066 A    2/1976    Green et al.
3,974,826 A    8/1976    Eggleton et al.
(Continued)

FOREIGN PATENT DOCUMENTS

EP    0894473    2/1999
EP    0961135    12/1999
(Continued)

OTHER PUBLICATIONS

US 5,924,990, 07/1999, Nachtomy et al. (withdrawn)
(Continued)

*Primary Examiner* — Bo J Peng
(74) *Attorney, Agent, or Firm* — Dykema Gossett PLLC

(57) ABSTRACT

Apparatus for generating an organ timing signal relating to an inspected organ within the body of a patient, including a medical positioning system, and a processor coupled with the medical positioning system, the medical positioning system including at least one reference electromagnetic transducer placed at a reference location, at least one inner electromagnetic transducer attached to a surgical tool inserted in a blood vessel in the vicinity of the inspected organ, and a medical positioning system processor coupled with the reference electromagnetic transducer and the inner electromagnetic transducer, the medical positioning system processor determining the three-dimensional position of the inner electromagnetic transducer, by processing transmitted electromagnetic signals transmitted from one of the reference electromagnetic transducer and the inner electromagnetic transducer with detected electromagnetic signals detected by the other of the reference electromagnetic transducer and the inner electromagnetic transducer, the medical positioning system processor further generating medical positioning system data sets, each of the medical positioning system data sets including a collection of three-dimensional
(Continued)

position coordinate readings demonstrating the motion trajectory of the surgical tool over time, the processor generating the organ timing signal from the medical positioning system data sets by detecting and identifying periodic motion frequencies in the medical positioning system data sets, and filtering the periodic motion frequencies from the medical positioning system data sets.

21 Claims, 10 Drawing Sheets

Related U.S. Application Data continuation-in-part of application No. 10/938,395, filed on Sep. 9, 2004, now Pat. No. 7,778,688, which is a continuation-in-part of application No. 09/949,160, filed on Sep. 7, 2001, now Pat. No. 7,343,195, which is a continuation-in-part of application No. 09/782,528, filed on Feb. 13, 2001, now Pat. No. 7,386,339, which is a continuation-in-part of application No. 09/314,474, filed on May 18, 1999, now Pat. No. 6,233,476.

(51) Int. Cl.
*A61B 5/00* (2006.01)
*A61B 34/10* (2016.01)
*A61B 5/113* (2006.01)
*A61B 6/03* (2006.01)
*A61B 6/00* (2006.01)
*A61B 8/08* (2006.01)
*A61B 8/12* (2006.01)
*A61B 5/06* (2006.01)
*A61B 90/00* (2016.01)

(52) U.S. Cl.
CPC .......... *A61B 5/1107* (2013.01); *A61B 5/1128* (2013.01); *A61B 5/721* (2013.01); *A61B 5/7275* (2013.01); *A61B 5/742* (2013.01); *A61B 6/032* (2013.01); *A61B 6/037* (2013.01); *A61B 6/504* (2013.01); *A61B 8/0841* (2013.01); *A61B 8/12* (2013.01); *A61B 34/10* (2016.02); *A61B 2034/107* (2016.02); *A61B 2034/2051* (2016.02); *A61B 2034/2065* (2016.02); *A61B 2034/2072* (2016.02); *A61B 2090/372* (2016.02)

(58) Field of Classification Search
CPC ....... A61B 5/1128; A61B 5/113; A61B 5/721; A61B 5/7275; A61B 5/742; A61B 6/032; A61B 6/037; A61B 6/504; A61B 8/0841; A61B 8/12; A61B 2034/107; A61B 2034/2051; A61B 2034/2065; A61B 2034/2072; A61B 2090/372
See application file for complete search history.

(56) References Cited

U.S. PATENT DOCUMENTS

| | | |
|---|---|---|
| 3,990,296 A | 11/1976 | Erikson |
| 4,398,540 A | 8/1983 | Takemura et al. |
| 4,737,794 A | 4/1988 | Jones |
| 4,794,931 A | 1/1989 | Yock |
| 5,016,642 A | 5/1991 | Dukes et al. |
| 5,152,290 A | 10/1992 | Freeland |
| 5,159,931 A | 11/1992 | Pini |
| 5,318,025 A | 6/1994 | DuMoulin et al. |
| 5,360,008 A * | 11/1994 | Campbell, Jr. ...... A61B 5/1135 128/902 |
| 5,398,691 A | 3/1995 | Martin |
| 5,445,150 A | 8/1995 | Dumoulin et al. |
| 5,453,686 A | 9/1995 | Anderson |
| 5,529,070 A | 6/1996 | Augustine et al. |
| 5,540,928 A | 7/1996 | Edelman et al. |
| 5,577,502 A | 11/1996 | Darrow et al. |
| 5,588,432 A | 12/1996 | Crowley et al. |
| 5,622,174 A | 4/1997 | Yamazaki |
| 5,638,819 A | 6/1997 | Manwaring et al. |
| 5,646,525 A | 7/1997 | Gilboa |
| 5,669,385 A | 9/1997 | Pesque et al. |
| 5,690,113 A | 11/1997 | Sliwa et al. |
| 5,704,361 A | 1/1998 | Seward et al. |
| 5,724,982 A | 3/1998 | Schnurer et al. |
| 5,729,129 A | 3/1998 | Acker |
| 5,730,129 A | 3/1998 | Darrow et al. |
| 5,740,808 A | 4/1998 | Panescu et al. |
| 5,744,953 A | 4/1998 | Hansen |
| 5,752,513 A | 5/1998 | Acker et al. |
| 5,787,889 A | 8/1998 | Edward et al. |
| 5,797,849 A | 8/1998 | Vesely et al. |
| 5,806,521 A | 9/1998 | Morimoto et al. |
| 5,810,008 A | 9/1998 | Dekel et al. |
| 5,823,958 A | 10/1998 | Truppe |
| 5,830,145 A | 11/1998 | Tenhoff |
| 5,830,222 A | 11/1998 | Makower |
| 5,833,608 A | 11/1998 | Acker |
| 5,840,025 A | 11/1998 | Ben-Haim |
| 5,846,200 A | 12/1998 | Schwartz |
| 5,899,860 A | 5/1999 | Pfeiffer et al. |
| 5,906,578 A | 5/1999 | Rajan et al. |
| 5,913,820 A | 6/1999 | Bladen et al. |
| 5,921,934 A | 7/1999 | Teo |
| 5,924,989 A | 7/1999 | Polz |
| 5,928,248 A | 7/1999 | Acker |
| 5,935,075 A | 8/1999 | Casscells et al. |
| 5,938,606 A | 8/1999 | Bonnefous |
| 5,949,491 A | 9/1999 | Callahan et al. |
| 5,955,879 A | 9/1999 | Durdle et al. |
| 5,957,844 A | 9/1999 | Dekel et al. |
| 5,967,980 A | 10/1999 | Ferre et al. |
| 5,976,088 A | 11/1999 | Urbano et al. |
| 5,993,390 A | 11/1999 | Savord et al. |
| 5,994,690 A | 11/1999 | Kulkarni et al. |
| 6,006,126 A | 12/1999 | Cosman |
| 6,016,439 A | 1/2000 | Acker |
| 6,030,343 A | 2/2000 | Chechersky et al. |
| 6,035,856 A | 3/2000 | LaFontaine et al. |
| 6,047,080 A | 4/2000 | Chen et al. |
| 6,134,003 A | 10/2000 | Tearney et al. |
| 6,148,095 A | 11/2000 | Prause et al. |
| 6,152,878 A | 11/2000 | Nachtomy et al. |
| 6,161,032 A | 12/2000 | Acker |
| 6,167,296 A | 12/2000 | Shahidi |
| 6,169,917 B1 | 1/2001 | Masotti et al. |
| 6,175,669 B1 | 1/2001 | Colston et al. |
| 6,185,271 B1 | 2/2001 | Kinsinger |
| 6,195,450 B1 | 2/2001 | Qian et al. |
| 6,210,168 B1 | 4/2001 | Aiger |
| 6,213,945 B1 | 4/2001 | Tynan |
| 6,216,029 B1 | 4/2001 | Paltieli |
| 6,228,028 B1 | 5/2001 | Klein et al. |
| 6,233,476 B1 | 5/2001 | Strommer et al. |
| 6,246,898 B1 | 6/2001 | Vesely et al. |
| 6,261,247 B1 | 7/2001 | Ishikawa et al. |
| 6,275,724 B1 | 8/2001 | Dickinson et al. |
| 6,317,621 B1 | 11/2001 | Graumann et al. |
| 6,321,109 B2 | 11/2001 | Ben-Haim et al. |
| 6,344,863 B1 | 2/2002 | Capelli et al. |
| 6,368,285 B1 | 4/2002 | Osadchy et al. |
| 6,381,350 B1 | 4/2002 | Klingensmith et al. |
| 6,385,476 B1 | 5/2002 | Osadchy et al. |
| 6,390,982 B1 | 5/2002 | Bova et al. |
| 6,405,072 B1 | 6/2002 | Cosman et al. |
| 6,416,476 B1 | 7/2002 | Ogasawara et al. |
| 6,423,009 B1 | 7/2002 | Downey et al. |
| 6,432,041 B1 | 8/2002 | Taniguchi et al. |
| 6,470,207 B1 | 10/2002 | Simon et al. |
| 6,498,944 B1 | 12/2002 | Ben-Haim et al. |

(56) References Cited

U.S. PATENT DOCUMENTS

| | | |
|---|---|---|
| 6,501,981 B1 | 12/2002 | Schweikard et al. |
| 6,546,271 B1 | 4/2003 | Reisfeld |
| 6,556,695 B1 | 4/2003 | Packer et al. |
| 6,587,707 B2 | 7/2003 | Nehrke et al. |
| 6,589,163 B2 | 7/2003 | Aizawa et al. |
| 6,618,612 B1 * | 9/2003 | Acker ............... A61B 5/06 128/899 |
| 6,626,902 B1 | 9/2003 | Kucharczyk et al. |
| 6,671,538 B1 | 12/2003 | Ehnholm et al. |
| 6,730,030 B2 | 5/2004 | Palti |
| 6,733,458 B1 | 5/2004 | Steins et al. |
| 6,773,393 B1 | 8/2004 | Taniguchi et al. |
| 6,775,404 B1 | 8/2004 | Pagoulatos et al. |
| 6,788,967 B2 | 9/2004 | Ben-Haim et al. |
| 6,895,267 B2 | 5/2005 | Panescu et al. |
| 6,917,827 B2 | 7/2005 | Kienzle, III |
| 7,007,699 B2 | 3/2006 | Martinelli et al. |
| 7,156,655 B2 | 1/2007 | Sachdeva et al. |
| 7,159,592 B1 | 1/2007 | Makower et al. |
| 7,195,587 B2 | 3/2007 | Taniguchi et al. |
| 7,197,354 B2 | 3/2007 | Sobe |
| 7,235,084 B2 | 6/2007 | Skakoon et al. |
| 7,263,397 B2 | 8/2007 | Hauck et al. |
| 7,343,195 B2 | 3/2008 | Strommer et al. |
| 7,386,339 B2 | 6/2008 | Strommer et al. |
| 7,398,116 B2 | 7/2008 | Edwards |
| 7,527,597 B2 | 5/2009 | Sandler et al. |
| 7,739,090 B2 | 6/2010 | Charbel et al. |
| 7,778,688 B2 | 8/2010 | Strommer |
| 7,881,769 B2 | 2/2011 | Sobe |
| 8,126,534 B2 | 2/2012 | Maschke |
| 8,332,013 B2 | 12/2012 | Strommer |
| 8,442,618 B2 | 5/2013 | Strommer et al. |
| 2001/0031919 A1 | 10/2001 | Strommer et al. |
| 2001/0044578 A1 | 11/2001 | Ben-Haim et al. |
| 2002/0007124 A1 | 1/2002 | Woodward |
| 2002/0049375 A1 | 4/2002 | Strommer et al. |
| 2002/0049735 A1 | 4/2002 | Matsumoto et al. |
| 2002/0193686 A1 | 12/2002 | Gilboa |
| 2003/0074011 A1 | 4/2003 | Gilboa et al. |
| 2003/0190064 A1 | 10/2003 | Inoue |
| 2004/0034297 A1 | 2/2004 | Darrow et al. |
| 2004/0097804 A1 | 5/2004 | Sobe |
| 2004/0116775 A1 | 6/2004 | Taniguchi et al. |
| 2004/0116813 A1 | 6/2004 | Selzer et al. |
| 2004/0138548 A1 * | 7/2004 | Strommer ............. A61B 5/0555 600/407 |
| 2004/0215071 A1 | 10/2004 | Frank et al. |
| 2005/0033149 A1 | 2/2005 | Strommer et al. |
| 2005/0049493 A1 | 3/2005 | Kerby et al. |
| 2005/0107688 A1 | 5/2005 | Strommer |
| 2005/0129176 A1 | 6/2005 | Kokubun et al. |
| 2005/0197557 A1 | 9/2005 | Strommer et al. |
| 2005/0197566 A1 | 9/2005 | Strommer et al. |
| 2006/0058647 A1 | 3/2006 | Strommer et al. |
| 2006/0064006 A1 | 3/2006 | Strommer et al. |
| 2006/0079745 A1 | 4/2006 | Viswanathan |
| 2006/0089706 A1 | 4/2006 | Plaia et al. |
| 2007/0287901 A1 | 12/2007 | Strommer et al. |
| 2008/0175463 A1 | 7/2008 | Strommer et al. |
| 2008/0221440 A1 | 9/2008 | Iddan et al. |
| 2008/0221442 A1 | 9/2008 | Tolkowsky et al. |
| 2009/0182224 A1 * | 7/2009 | Shmarak ............... A61B 5/061 600/424 |
| 2010/0331950 A1 | 12/2010 | Strommer |
| 2011/0230758 A1 | 9/2011 | Eichler |

FOREIGN PATENT DOCUMENTS

| | | |
|---|---|---|
| EP | 1005835 | 6/2000 |
| EP | 1088515 | 4/2001 |
| JP | 62032304 | 2/1987 |
| JP | 8500441 | 1/1996 |
| JP | 11110114 | 4/1999 |
| JP | 1999151246 | 6/1999 |
| JP | 11197159 | 7/1999 |
| JP | 2000023984 | 1/2000 |
| JP | 2000166927 | 6/2000 |
| JP | 2000279425 | 10/2000 |
| JP | 2001170027 | 6/2001 |
| JP | 2002200058 | 7/2002 |
| JP | 2003520062 | 7/2003 |
| JP | 2004533863 | 11/2004 |
| JP | 2007502187 | 2/2007 |
| JP | 2010507104 | 3/2010 |
| JP | 4701179 | 6/2011 |
| WO | WO-9404938 | 3/1994 |
| WO | WO-96/05768 | 2/1996 |
| WO | WO-96/41119 | 12/1996 |
| WO | WO-97/29682 | 8/1997 |
| WO | WO-97/29685 | 8/1997 |
| WO | WO-97/36143 | 10/1997 |
| WO | WO-9811524 | 3/1998 |
| WO | WO-9900052 | 1/1999 |
| WO | WO-99/43253 | 9/1999 |
| WO | WO-00/10456 | 3/2000 |
| WO | WO-00/16684 | 3/2000 |
| WO | WO 0069335 | 11/2000 |
| WO | WO-02/064011 | 8/2002 |
| WO | WO-03/059167 | 7/2003 |
| WO | WO-2004/060157 | 7/2004 |
| WO | WO-2004/062501 | 7/2004 |
| WO | WO 2004103174 | 12/2004 |
| WO | WO-2005/039391 | 5/2005 |
| WO | WO 2008047992 | 4/2008 |

OTHER PUBLICATIONS

Panza, Julio A., "Real-time three-dimensional echocardiography: An overview", *The International Journal of Cardiovascular Imaging* 17:227-235, 2001.

Solomon, et al., "Real-Time Bonchoscope Tip Localization Enables Three-Dimensional CT Image Guidance for Transbronchial Needle Aspiration in Swine", Laboratory and Animal Investigation, vol. 114, Issue 5, Nov. 1998, pp. 104-1410.

* cited by examiner

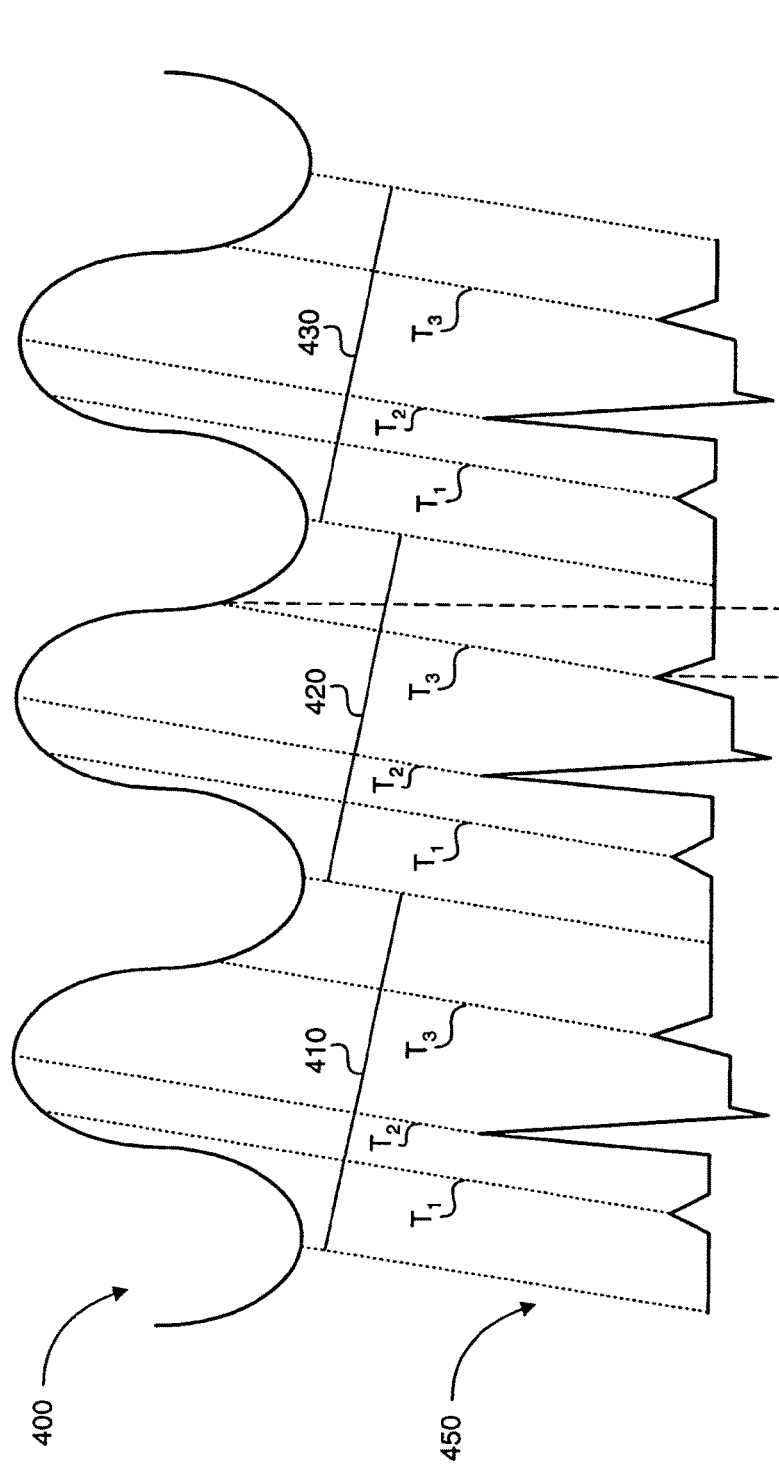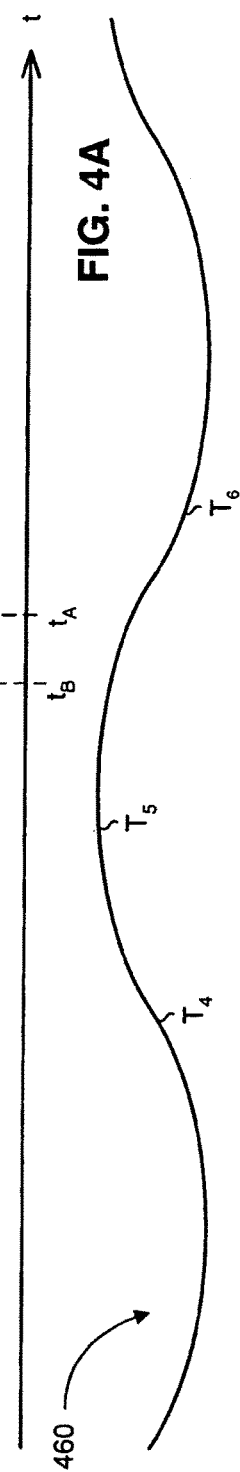

METHOD AND APPARATUS FOR INVASIVE DEVICE TRACKING USING ORGAN TIMING SIGNAL GENERATED FROM MPS SENSORS

CROSS-REFERENCE TO RELATED APPLICATIONS

The present application is a continuation of U.S. application Ser. No. 10/986,567(the '567 application), filed 10 Nov. 2004, now U.S. Pat No. 9,572,519, which is a continuation-in-part of U.S. application Ser. No. 10/938,395 (the '395application), filed 09 Sep. 2004, now U.S. Pat. No. 7,778,688. This application is related to U.S. application Ser. No. 09/949,160 (the '160application), filed 07 Sep. 2001, now U.S. Pat. No. 7,343,195, U.S. application Ser. No. 09/782,528 (the '528 application), filed 13 Feb. 2001, now U.S. Pat No. 7,386,339, and U.S. application Ser. No. 09/314,474 (the '474 application), filed 18 May 1999, now U.S. Pat. No. 6,233,476. The '567 application, the '395 application, the '160 application, the '528 application, and the '474 application are all hereby incorporated by reference in their entirety as though fully set forth herein.

FIELD OF THE DISCLOSED TECHNIQUE

The disclosed technique relates to medical diagnostics and surgery systems and methods in general, and to a method and system for monitoring organ phases in three-dimensional medical imaging and navigation, in particular.

BACKGROUND OF THE DISCLOSED TECHNIQUE

Medical imaging is a powerful tool to assist in the performance of various types of medical operations, and to enhance diagnostics and other decisions concerning a medical procedure. Several systems are known in the art to produce real-time medical images via a variety of different imaging modalities. In instances of imaging of anatomical structures that involve periodic motion or cyclic phases, the imaging system may encompass a timing element to take this into account. Monitoring devices, such as an electrocardiogram (ECG) machine, are regularly incorporated into medical imaging systems to provide timing information for registering the captured images with respect to organ phase. Typically, the timing information obtained from such monitoring devices is not completely accurate. As well, the signal received from such monitoring devices involves a delay, and is not obtained in real-time with respect to the actual organ motion. Finally, an external monitoring device adds a cumbersome element to an already complex system.

U.S. Pat. No. 5,577,502 to Darrow et al entitled "Imaging of interventional devices during medical procedures", is directed to a method for compensation of subject motion during tracking of an invasive device within the body of the subject. A device tracking unit determines the location of the invasive device relative to a fixed reference point. An imaging device acquires a reference image of the subject. A position detection means placed within the imaging device measures the location over time of a reference point of the subject. Each acquired image is stored together with the corresponding location of subject reference point. A subject tracking unit receives location information over time from position detection means, and computes translation and rotation movement of the subject from time of image acquisition to time of device location measurement. A registration unit receives the reference image, the net position and orientation change of the subject, and the device location. The registration unit translates and rotates the reference image to match the position and orientation of subject at the time of device location measurement. An image of the device is superimposed upon the translated/rotated image of the subject at its absolute position and orientation. The registration unit may also adjust the displayed location of the device, rather than the display of the image.

In addition to translation and rotation motion, the registration unit accounts for expansion and contraction of the subject, occurring due to a periodic motion cycle, such as the respiratory or cardiac cycles. Position detection means measures the change in the subject due to expansion and contraction, and feeds this information to the registration unit. The registration unit distorts the reference image in accordance with the expansion and contraction, and subsequent translation and rotation, thereby dynamically registering the image of the subject with the current device location.

Alternatively, the imaging device may monitor subject motion by obtaining subsequent projections of the subject and then detecting offset and cross-sectional size of the subject in these images. Further alternatively, a series of reference images are each gated to the periodic motion cycle. The imaging device acquires a series of images at different times within the cardiac cycle, as measured by an ECG signal. An ECG provides a signal for each measurement of device location. At a given time, an image from the series which corresponds to the ECG signal is selected as the reference image. The registration unit translates and rotates this reference image, with respect to the information received from the subject tracking unit for that time. A representation of the measured location of the device is superimposed upon the updated image, resulting in a registered image of the subject and the invasive device.

U.S. Pat. No. 5,622,174 to Yamazaki entitled "Ultrasonic diagnostic apparatus and image displaying system", is directed to a system for determining movement velocities of a moving internal organ and providing a color display of the movement velocities over time. An ultrasonic probe transmits an ultrasound beam toward the heart. The transmitted ultrasonic beam is partially reflected by tissues of the heart as an echo signal and returned to the probe. The echo signal has a Doppler shift in frequency due to the Doppler effect. The echo signal is transduced into a voltage signal and supplied to a reception signal processor. The signal is beam-formed, detected and output to a B-mode digital scan converter (DSC). The B-mode DSC converts the image data of the signal to standard television scanning data, which is sent to an image synthesizer. The B-mode DSC also stores a plurality of image data at arbitrary cardiac timing in a B-mode frame memory.

The reception signal processor also sends the transduced echo signal to a phase detector. The phase detector performs phase detection on the Doppler shift frequency to extract the Doppler shift signal. A low pass filter filters out unnecessary Doppler signals resulting from valve motion or blood flow, leaving only the Doppler signal from the cardiac muscle. A frequency analyzer calculates physical values relating to the velocities at each sampling volume of a scan plane, using the Fast Fourier Transform (FFT) or auto-correlation method. These values include mean Doppler frequencies (corresponding to mean velocities of movement of the organ), variance (turbulence factors of Doppler spectrum), and maximum values of Doppler shift frequencies (maximum velocities of organ movement at sampling volume). These values are sent as color Doppler information to a vector-velocity calculator, which calculates the absolute movement velocities of the organ at each sampling volume point. A display presents the magnitude and/or direction of velocities, in accordance with a color scheme assignment. It is noted that detected ECG signals of the heart are used to trigger the signal generator (output reference pulses for transmission/reception of ultrasonic beams). In addition, these cardiac timing signals are used to produce a real-time image displaying changes in movement velocities of the heart in color.

U.S. Pat. No. 6,246,898 to Vesely et al entitled "Method for carrying out a medical procedure using a three-dimensional imaging and tracking system", is directed to a method for performing an in-vivo medical procedure on an associated body using three-dimensional tracking and imaging. A plurality of transceivers is used to track the three-dimensional motion of an object under investigation. At least four transceivers are implanted within a specimen in whom distances are to be measured. Three transceivers lie in a (x,y) plane and act as a reference. The fourth transceiver determines the z-coordinates of surrounding transducers by determining if an active one of the transducers lies above or below the reference plane established by the three transceivers. Each of a plurality of transmitters attached to the specimen at various locations is sequentially fired, while the three reference transceivers record the receiver signals. Since the difference from each transmitter to the reference plane is known, the relative x,y,z coordinates of the transmitters can be determined using triangulation.

The video display is synchronized with the real-time patient heart beat using an ECG signal. An Analog-to-Digital (ND) converter converts the ECG signal into digital data. A sync generator module produces a timing signal corresponding to the current heart activity from the digital ECG data. This is done by activating a memory location or input port, or generating an interrupt, at the precise time a QRS complex is identified. In particular, the sync generator module tests the data signal for large rates of change, zero crossings, and other information allowing the sync generator module to reveal the QRS complex of the signal U.S. Pat. No. 6,556,695 to Packer et al entitled "Method for producing high resolution real-time images, of structure and function during medical procedures", is directed to a method for providing medical images in real-time to assist physicians in the performance of medical procedures. A Medical Resonance Imaging (MRI) system obtains a high resolution model of the heart prior to the medical procedure. Images of the heart are acquired during successive cardiac phases. A pulse generator creates a series of fast gradient echo pulse sequences. The R-R interval of the cardiac cycle is divided up into several short segments of pulse sequences, using an ECG gating signal that triggers at the peak of the R wave. A single coordinate, or view, of the heart is acquired during each fast gradient echo segment. Adjacent segments are combined into groups, and the data in each group contributes to generating an image at a different phase of the cardiac cycle. A number (e.g., fifteen) of two-dimensional slices are acquired during an entire cardiac cycle, depicting one slice through the heart at (e.g., fifteen) successive phases of the cardiac cycle. Additional slices of the heart are acquired and reconstructed into two-dimensional images. These two-dimensional slices are then combined to form (e.g., fifteen) three-dimensional image data sets.

During the medical procedure, an ultrasonic transducer acquires low-resolution image frames of the heart in real-time. An ECG signal from the patient detects the real-time cardiac phase. The stored high-resolution heart model is registered using the real-time image frames and ECG signal. The registered high-resolution model is then used to produce high-resolution, large field of view images in real-time on a display.

SUMMARY OF THE DISCLOSED TECHNIQUE

It is an object of the disclosed technique to provide a novel method and apparatus for intra-body navigation and invasive device tracking using an organ timing signal, which is generated without an external monitoring device.

In accordance with the disclosed technique, there is thus provided an apparatus for generating an organ timing signal relating to at least one inspected organ within the body of a patient. The apparatus includes a medical positioning system (MPS) and a processor. The processor is coupled with the MPS. The MPS includes at least one reference electromagnetic transducer, at least one inner electromagnetic transducer, and an MPS processor. The MPS processor is coupled with the reference electromagnetic transducer and with the inner electromagnetic transducer. The inner electromagnetic transducer is attached to a surgical tool inserted in a blood vessel in the vicinity of the inspected organ. The MPS processor determines the three-dimensional position of the inner electromagnetic transducer, by processing transmitted electromagnetic signals transmitted from one of the reference electromagnetic transducer and the inner electromagnetic transducer with detected electromagnetic signals detected by the other of the reference electromagnetic transducer and the inner electromagnetic transducer. The MPS processor further generates MPS data sets. Each of the MPS data sets includes a collection of three-dimensional position coordinate readings demonstrating the motion trajectory of the surgical tool over time. The processor generates the organ timing signal from the MPS data sets by detecting and identifying periodic motion frequencies in the MPS data sets, and filtering the periodic motion frequencies from the MPS data sets.

According to the disclosed technique, there is also provided a method for generating an organ timing signal relating to an inspected organ within the body of a patient. The method includes the procedures of transmitting electromagnetic signals and detecting the electromagnetic signals, processing the transmitted electromagnetic signals with the detected electromagnetic signals, and determining the three-dimensional position of a surgical tool inserted within the body of a patient based on the processing. The method further includes the procedures of generating MPS data sets comprising a collection of three-dimensional position coordinate readings demonstrating the motion trajectory of the surgical tool over time, detecting and identifying periodic motion frequencies in the MPS data sets, and filtering the periodic motion frequencies from the MPS data sets.

BRIEF DESCRIPTION OF THE DRAWINGS

The disclosed technique will be understood and appreciated more fully from the following detailed description taken in conjunction with the drawings in which:

FIG. 4A is a schematic illustration of a sample cardiac trajectory, in electrical signal representation and in mechanical signal representation;

FIG. 4B is a schematic illustration of a sample respiratory trajectory in mechanical signal representation;

DETAILED DESCRIPTION OF THE EMBODIMENTS

The disclosed technique overcomes the disadvantages of the prior art by providing methods and apparatus for intra-body navigation and invasive device tracking using an organ timing signal generated without an external monitoring device. It is noted that the terms "phase" and "activity-state" are used interchangeably herein below. According to one embodiment, phase information is generated from a sensor which concurrently provides position and orientation information. The system allows for image acquisition and playback, three-dimensional model reconstruction, intra-body navigation, and tracking an invasive device during minimally invasive surgery. These aspects are further explained in US Patent Application 2002/0049375 to Strommer et al entitled "Method and apparatus for real time quantitative three-dimensional image reconstruction of a moving organ and intra-body navigation", which is hereby incorporated by reference. Also, the system can be used to optimally advise on the type and dimensions of surgical tool to insert, where the surgical tool should be inserted, and other decisions related to a surgical procedure.

Figure 1:
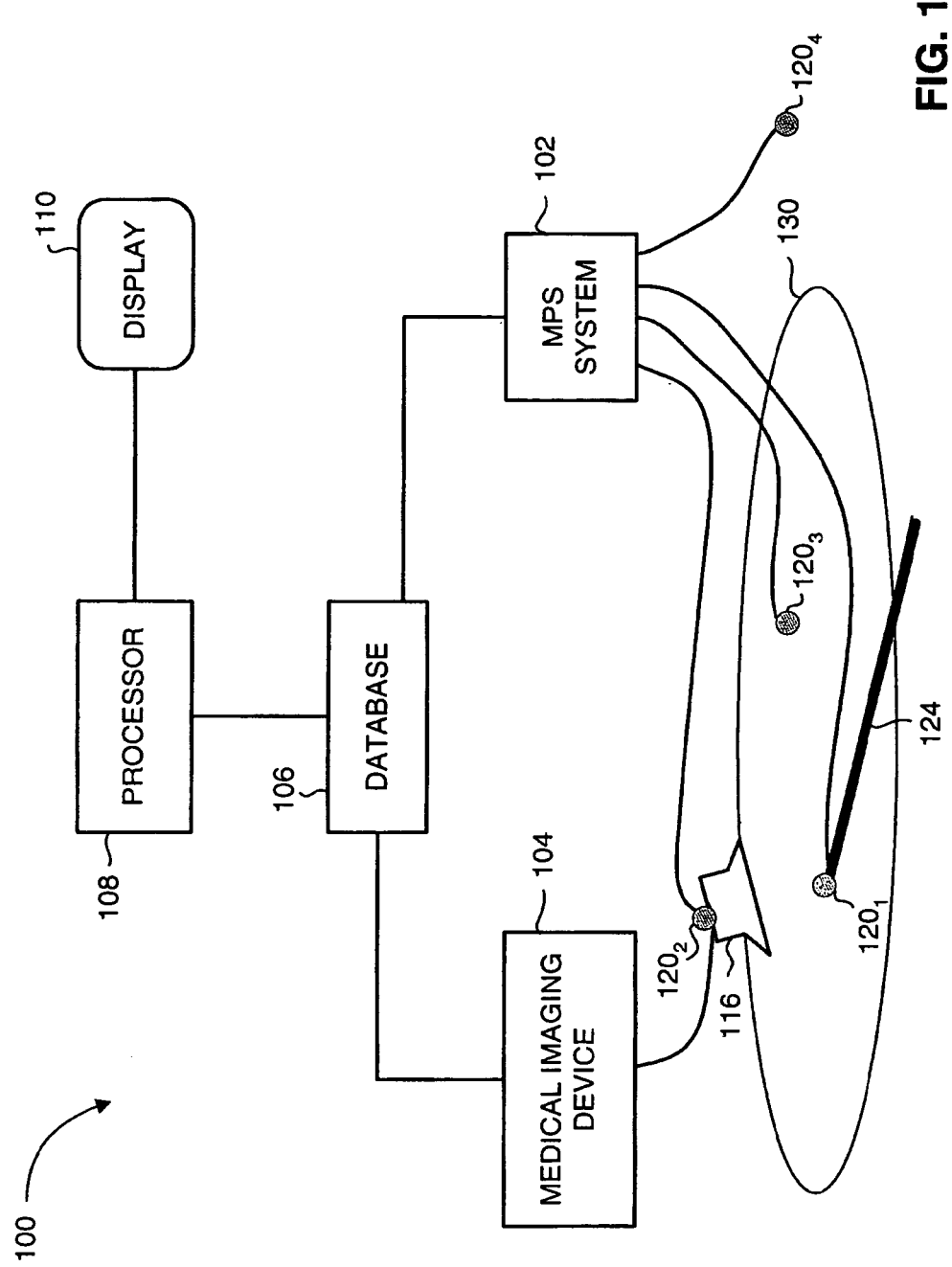
FIG. 1 is a schematic illustration of a system, constructed and operative in accordance with an embodiment of the disclosed technique.

Reference is now made to FIG. 1, which is a schematic illustration of a system, generally referenced 100, constructed and operative in accordance with an embodiment of the disclosed technique.

System 100 includes a Medical Positioning System (MPS) 102, a medical imaging device 104, a database 106, a processor 108, a display 110, an image detector 116, a plurality of MPS sensors $120_1$, $120_2$, $120_3$ and $120_4$, and a surgical tool 124. MPS 102 and medical imaging device 104 are coupled with database 106. Processor 108 is coupled with database 106 and display 110. MPS 102 includes plurality of MPS sensors $120_1$, $120_2$, $120_3$, and $120_4$. Medical imaging device 104 includes image detector 116.

MPS 102 receives and processes data related to the position of an area of the body of a patient. It is noted that henceforth the term "position" refers to either the location or positional coordinate of a point in space, the orientation of that point in space, or both. The data is obtained via plurality of MPS sensors $120_1$, $120_2$, $120_3$, and $120_4$. MPS sensor $120_1$ is attached to surgical tool 124. MPS sensor $120_2$ is attached to image detector 116. MPS sensor $120_3$ is generally attached to an inspected area of a patient body (referenced 130). MPS sensor $120_4$ is generally attached to a known area on the surface on which the patient rests.

Each of MPS sensors $120_1$, $120_2$, $120_3$, and $120_4$ contain electromagnetic field detection elements, such as coils. MPS 102 produces predetermined electromagnetic fields, which are detected by MPS sensors $120_1$, $120_2$, $120_3$, and $120_4$, respectively. MPS 120 processes the detected electromagnetic fields, and obtains an indication of the three-dimensional position of MPS sensors $120_1$, $120_2$, $120_3$, and $120_4$. In this manner, MPS 102 determines the three-dimensional position of image detector 116, surgical tool 124, a selected area of patient body 130, and a known area on the surface on which the patient rests. It is noted that the electromagnetic transmission may be reversed, such that the field detection elements are stationary and located in MPS 102 while predetermined electromagnetic fields are produced by MPS sensors $120_1$, $120_2$, $120_3$, and $120_4$. A medical positioning system such as MPS 102 is explained further in U.S. Pat. No. 6,233,476 to Strommer et al entitled "Medical positioning system", which is hereby incorporated by reference.

In one embodiment of the disclosed technique, each of MPS sensors $120_1$, $120_2$, $120_3$, and $120_4$ may be an electromagnetic transducer, capable of both transmitting an electromagnetic field and detecting an electromagnetic field. In addition, MPS 102 contains at least one reference electromagnetic transducer (not shown) which is placed at a certain reference location. The reference electromagnetic transducer may be one of MPS sensors $120_1$, $120_2$, $120_3$, and $120_4$. MPS 102 further contains an MPS processor (not shown) coupled with the reference electromagnetic transducer and each of the other electromagnetic transducers. The reference transducer then transmits predetermined electromagnetic signals in the form of electromagnetic fields, which are detected by MPS sensors $120_1$, $120_2$, $120_3$, and $120_4$, respectively. Alternatively, the electromagnetic transmission is reversed, such that predetermined electromagnetic signals are transmitted by MPS sensors $120_1$, $120_2$, $120_3$, and $120_4$, respectively, and are detected by the reference transducer. The MPS processor processes the detected electromagnetic signals, and obtains an indication of the three-dimensional position of MPS sensors $120_1$, $120_2$, $120_3$, and $120_4$. In this manner, MPS 102 determines the three-dimensional position of image detector 116, surgical tool 124, a selected area of patient body 130, and a known area on the surface on which the patient rests.

The position of image detector 116, obtained via MPS sensor $120_2$, is used in determining parameters (i.e., external optical parameters) relating to medical imaging device 104. It is noted that the parameters relating to medical imaging device 104 may also be obtained by other means, such as pre-known calibration target or fiducial points and the relationship of these points to their corresponding identified image.

The position of the patient body, obtained via MPS sensor $120_3$, is used as a reference to compensate for arbitrary patient movement. The data from MPS sensor $120_3$ is used to determine motion of the patient with respect to a known set of coordinates, such as the origin of the magnetic coordinate system or with respect to another sensor, or a set plurality of sensors, such as MPS sensor $120_4$. It is noted that each of MPS sensors $120_3$ and $120_4$ may be used individually to determine patient movement, or they may be used both together. It is further noted that either of MPS sensors $120_3$ or $120_4$ may include a plurality of sensors (i.e., there may be a plurality of sensors attached to an inspected area of patient body 130, and there may be a plurality of sensors attached to a known area on the surface on which the patient rests).

The process of compensating for patient movement or movement of medical imaging device 104 is known as coordinate system normalization. Coordinate system normalization, also referred herein below as "normalization", is done using the corresponding reference sensors (i.e., MPS sensors $120_3$ or $120_4$) for compensating patient movement. Compensating for movement of medical imaging device 104 may further utilize MPS sensor $120_2$ attached to image detector 116 on medical imaging device 104, in addition to MPS sensors $120_3$ or $120_4$. It is noted that normalization allows for the utilization of data sets among different sessions or medical procedures. The term "medical procedure" refers to any type of medical procedure performed on a patient, such as diagnostic, therapeutic, or preventative procedures. A medical procedure may be done in several stages. Each stage in a single medical procedure is known as a "session". It is further noted that no nullification of MPS sensor readings are required due to coordinate system normalization. All data readings obtained from MPS sensors $120_1$ and $120_2$ may be used for processing, with no need to dismiss a "faulty" reading as a result of arbitrary patient motion. It is yet further noted that coordinate system normalization allows for representing MPS data in different coordinate systems. For example, data may be represented with respect to the coordinate system of the patient, whereby the body of the patient is stationary, and the inspected organ and the surgical tool move. Alternatively, data may be represented with respect to the coordinate system of the inspected organ, whereby the inspected organ is stationary, and the body of the patient and the surgical tool move. Further alternatively, data may be represented with respect to the coordinate system of the surgical tool, whereby the surgical tool is stationary, and the body of the patient and the inspected organ move.

MPS 102 may include additional MPS sensors to be used as further references, similar to MPS sensor $120_3$ or MPS sensor $120_4$, thereby further assisting with coordinate system normalization. It is noted however, that other methods for assigning a reference point can be used, such as initial referencing between all MPS sensors and strapping the patient during the entire medical procedure, analyzing the acquired images and identifying a recurring visual point or section therein for each of the MPS sensors other than the sensor attached to the transducer, and the like.

MPS 102 also provides data for obtaining phase information relating to the activity state of an inspected organ. For example, if the inspected organ is a heart, phase information may be heart timing signals denoting stages within a cardiac cycle. A cardiac cycle is defined as the time between two subsequent heart contractions. The electrical activity of the heart as a function of time, such as electrical timing signals obtained by an ECG monitor, can reveal the current stage or phase of the heart within the cardiac cycle. Alternatively, if the inspected organ is a lung, phase information may relate to respiratory rate and stages of the lung within a respiratory cycle. For example, if the inspected organ is an eye, phase information may relate to movement of the eyelid and related ophthalmologic features. Processor 108 obtains phase information by processing data provided by MPS 102 via MPS sensor $120_1$, without the need for any external monitoring device (such as an ECG device). Other sensors may be used independently or in addition in order to generate phase information (e.g., MPS sensor $120_3$ in conjunction with MPS sensor $120_1$).

Medical imaging device 104 provides a two-dimensional image of an area within the body of the patient. In the example set forth herewith, the area inspected is the heart and surrounding blood vessels. Medical image device 104 can include any type of image acquisition system known in the art, such as ultra-sound, inner-vascular ultra-sound, X-ray, C-Arm machines (equipped with such devices), fluoroscopy, angiography, computerized tomography, nuclear magnetic resonance, positron-emission tomography, single-photon-emission tomography, and the like.

Medical imaging device 104 acquires a two-dimensional image via image detector 116. Image detector 116 detects a plurality of two-dimensional images, each representing a view of the inspected organ (e.g., the heart). MPS sensor $120_2$ attached to image detector 116 obtains information relating to the position of image detector 116. A frame grabber (not shown) acquires the images and provides them to database 106.

Database 106 stores data required by system 100. Database 106 is typically a database unit, which allows for storage and access of data records. The data includes frames of captured two-dimensional images from medical imaging system 104, as well as MPS sensor readings from MPS 102. Data is transferred to database 106, from which the data is recalled for processing. Intermediate and final data values obtained throughout computations of processor 108 may also be stored in database 106. Database 106 may further store information from additional devices used in conjunction with system 100 (e.g., information from an external monitoring device such as an ECG, intravascular ultrasound information, and the like). In general, database 106 stores all possible information that may be needed by system 100.

Data elements that are stored in database 106 are time-tagged. The term "time-tagging" herein below refers to the process of associating a data element with the exact time at which that data element was obtained (e.g., associating an MPS coordinate reading with the exact time at which that reading was obtained). The data obtained via each of plurality of MPS sensors $120_1$, $120_2$, $120_3$ and $120_4$ is time-tagged. The plurality of two-dimensional images acquired by medical imaging device 104 is also time-tagged. The time-tags are taken into account when processing the data elements stored in database 106.

Latency compensation is performed on all the time-tagged data elements. In general, image frames from the set of 2D images acquired by medical imaging device 104 are shifted so that the time-tags thereof match the time-tag of the corresponding MPS data set (i.e., images acquired at the same time as an MPS coordinate reading was obtained will be matched with one another).

Processor 108 operates on data gathered in database 106. Processor 108 performs necessary calculations, correlates between the different data streams, and performs filtering, segmentation, reconstruction io of three-dimensional models, and other operations. Processor 108 associates between captured two-dimensional images, position information relating to the respective images, and phase information relating to the respective images. Processor 108 constructs trajectories of surgical tool 124 guided within the body of a patient, respective of different activity-states of an inspected organ. Processor 108 may further construct a three-dimensional image from captured two-dimensional images having the same activity-state, and from three-dimensional position data associated with each of the images.

Display 110 presents a motion picture, or image sequence, of the inspected organ in real-time. The motion picture consists of the two-dimensional images captured by medical imaging device 104, with the three-dimensional position data of surgical tool 124 obtained by MPS 102 superimposed via optical projection. The motion picture may consist of a projection of a constructed three-dimensional model of the organ. The motion picture displays the trajectory of surgical tool 120 as the surgical tool is guided within the patient body, respective of different activity-states of an inspected organ. Display 110 may present a selected image frame of the motion picture respective of the real-time detected organ activity-state. Display 110 may provide different playback effects, freeze frames, change speed, select features, and the like. For example, display 110 may present a playback of previous images in a sequence, showing the progress of surgical tool during previous activity states of the organ. Display 110 may include multiple monitors, or separate windows within a single monitor, where each monitor or window presents a different view. For example, one monitor or window presents the current real-time three-dimensional position data of surgical tool 124 superimposed on the current image frame of the inspected organ respective of the current activity-state, while another monitor or window presents the current real-time three-dimensional position data of surgical tool 124 superimposed on a previous image frame (or image sequence) of the inspected organ respective of a previous activity-state (or activity-states). Display 110 may be a two-dimensional display, an auto-stereoscopic display to be viewed with a suitable pair of spectacles, a stand alone stereoscopic display, a pair of goggles, and the like.

Figure 2:
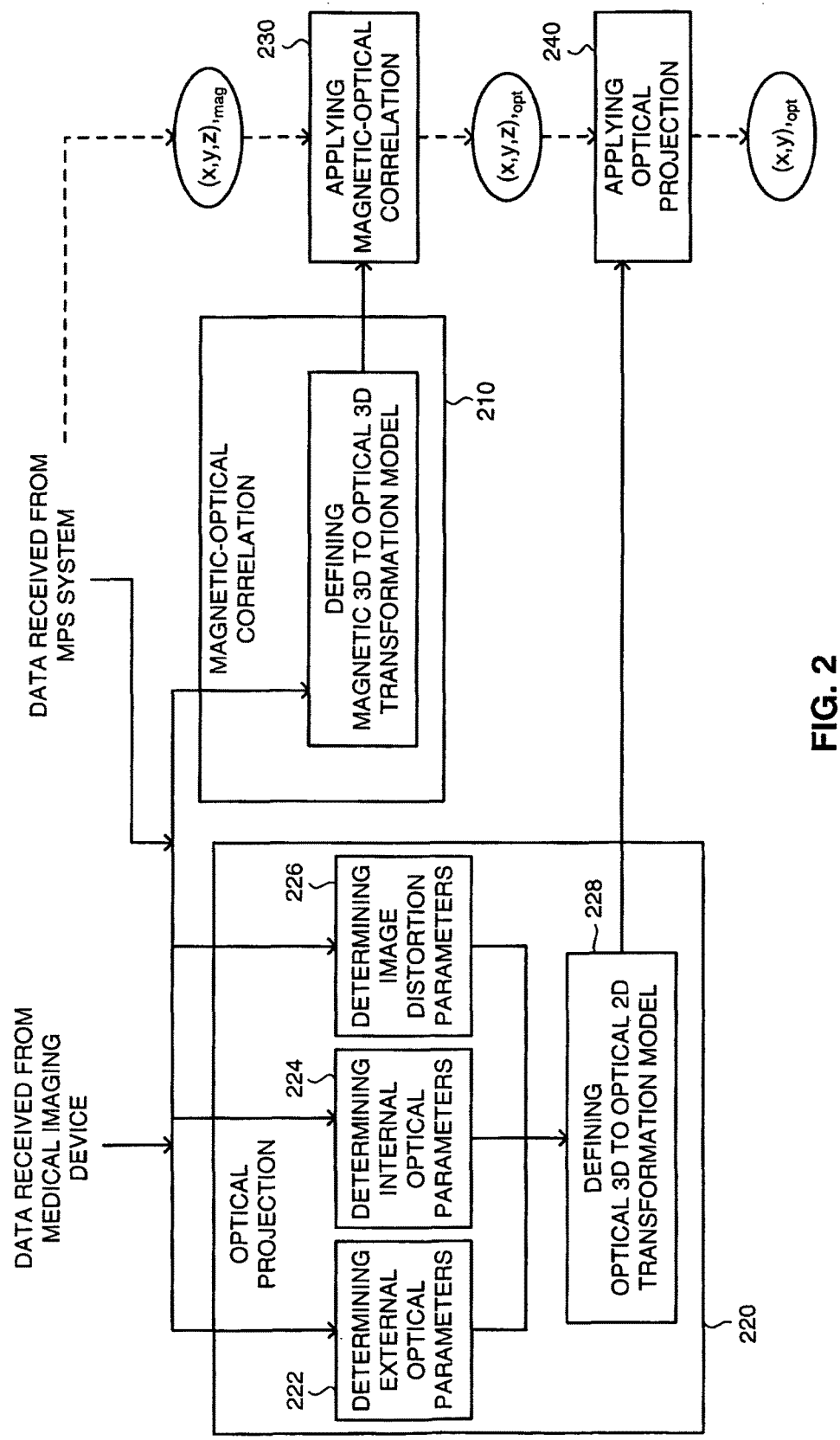
FIG. 2 is a block diagram of a method for registering three-dimensional magnetic coordinates into two-dimensional optical coordinates, operative in accordance with another embodiment of the disclosed technique.

Reference is now made to FIG. 2, which is a block diagram of a method for registering three-dimensional magnetic coordinates into two-dimensional optical coordinates, operative in accordance with another embodiment of the disclosed technique.

In procedure 210, a transformation model for magnetic-optical correlation is determined. Magnetic-optical correlation involves the conversion of three-dimensional magnetic coordinates, obtained from MPS sensors, into three-dimensional optical coordinates. The correlation procedure is generally performed once, during the initialization of the entire system. Procedure 210 involves defining a transformation model between the magnetic coordinate system and the optical coordinate system. This transformation defines a global solution of the working volume and does not require any further manual calibration or correlation. In general, as long as there is no change in the magnetic configuration parameters, correlation need not be repeated. The correlation may be modified automatically during the medical procedure in order to calibrate minor changes between the magnetic and optical coordinate systems.

In procedure 220, a transformation model for optical projection is determined. Optical projection involves the conversion of three-dimensional optical coordinates (obtained using magnetic-optical correlation) into two-dimensional optical coordinates, to be superimposed on an image displayed by display 110. Optical projection is based on a transformation model from a three-dimensional coordinate system to a two-dimensional coordinate system. This transformation model is based on external optical parameters, internal optical parameters, and image distortion parameters of medical imaging device 104. Procedure 220 consists of procedures 222, 224, 226, and 228.

In procedure 222, external optical parameters are determined. External optical parameters relate to the position of the medical imaging device 104. In particular, external optical parameters define the coordinate system of medical imaging device 104 with respect to the defined optical coordinate system. In procedure 224, internal optical parameters are determined. Internal optical parameters of the medical imaging device 104 relate to the image acquisition mechanism. For example, internal optical parameters may include: lens center point, focal length and the like. In procedure 226, image distortion parameters are determined. Image distortion parameters relate to parameters which alter the original proportion of objects as they appear in the images acquired by medical imaging device 104, as a result of physical characteristics of the image acquisition mechanism and the way that the image acquisition mechanism operates. Image distortion parameters may be computed either as a part of the internal optical parameters or as an additional set of correction parameters.

It is noted that the external optical parameters are usually calculated continuously in real-time, whereas it is generally sufficient to compute the internal optical parameters and image distortion parameters once during the beginning stages of the medical procedure. However, there may be cases when it is necessary to re-calculate the internal optical parameters and image distortion parameters at a later stage. MPS data may also be used in re-calculating the external optical parameters, internal optical parameters, and image distortion parameters of medical imaging device 104. In procedure 228, a transformation between the three-dimensional coordinate system and two-dimensional coordinate system is defined based on external optical parameters, internal optical parameters, and image distortion parameters of medical imaging device 104.

Alternatively, or in addition, a direct translation between the 3D MPS coordinate system and the image plane 2D coordinate system can be determined based on known MPS coordinate readings and their relationship to their corresponding identified image coordinates. It is noted that projection procedure 220 takes into account the time-tagged data from the reference sensors of the MPS data to be projected and the images to be projected upon. In case patient movement occurred after an image was acquired, or in case movement of medical imaging device 104 occurred after MPS data was taken, the reference sensors are used in order to compensate for either movements and ensure that the MPS data is projected accurately.

The method of FIG. 2 also includes procedures for converting a set of three-dimensional magnetic coordinates to two-dimensional optical coordinates, shown with reference to the dashed lines. Three-dimensional magnetic coordinates representing position data is obtained from MPS 102. In procedure 230, magnetic-optical correlation is applied to three-dimensional magnetic coordinates to produce the equivalent three-dimensional optical coordinates. In procedure 240, optical projection is applied to the three-dimensional optical coordinates to produce the equivalent two-dimensional optical coordinates. Alternatively a direct transformation from the MPS coordinate system to the image plane can be used. The two-dimensional optical coordinates may be shown on display 110, in context of the appropriate image frame of the motion picture. The MPS data is projected onto the image plane including all the needed distortion and conversions which affect the projection coordinates only.

Figure 3:
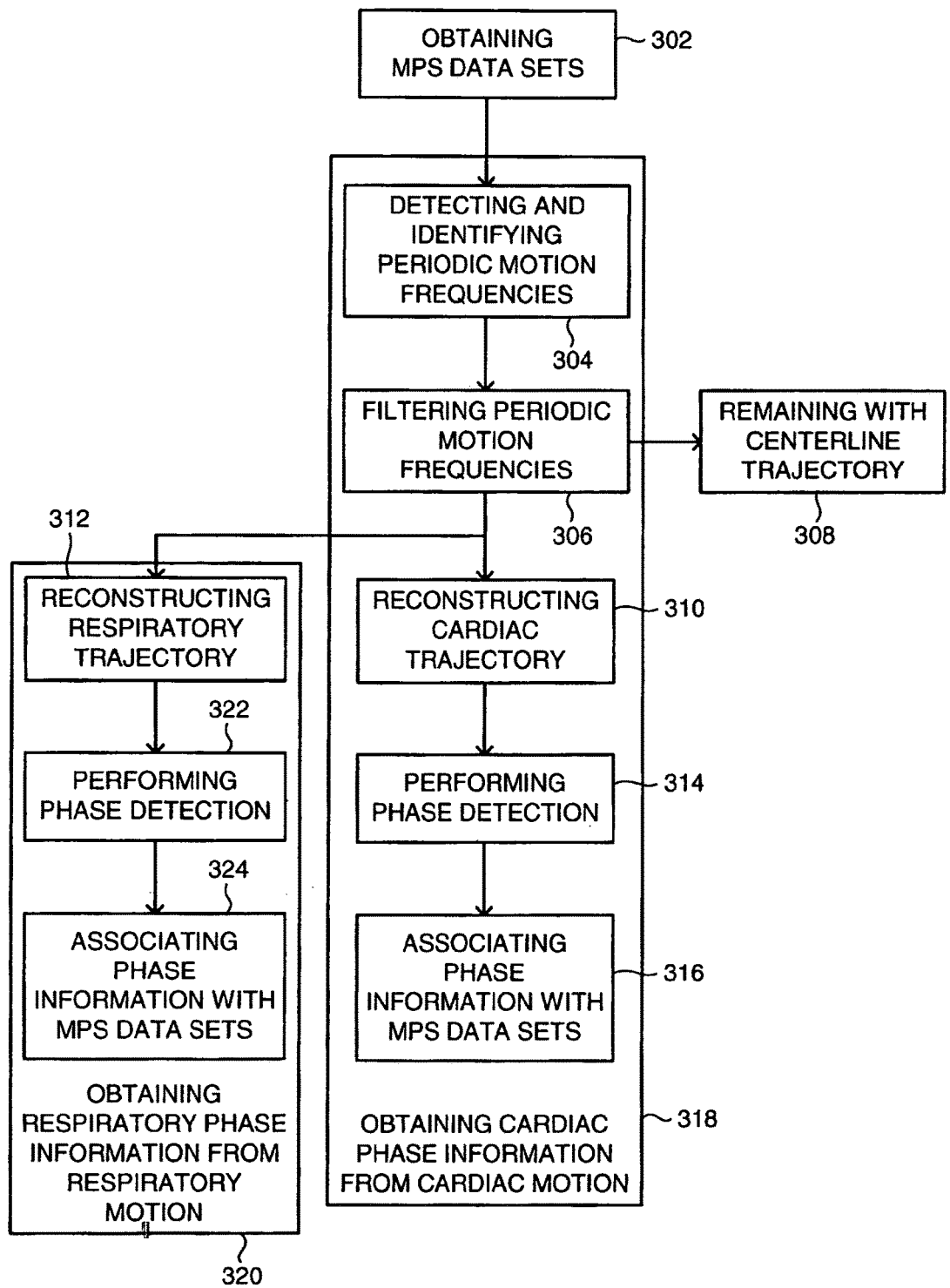
FIG. 3 is a block diagram of a method for obtaining phase information from MPS data sets, operative in accordance with a further embodiment of the disclosed technique.

Reference is now made to FIG. 3, which is a block diagram of a method for obtaining phase information from MPS data sets, operative in accordance with a further embodiment of the disclosed technique. In procedure 302, data sets are obtained from MPS 102. Each MPS data set comprises a series of position coordinate readings of image detector 116, surgical tool 124, a selected area of patient body 130, or a known area on the surface on which the patient rests, respectively, as received from one of plurality of MPS sensors $120_1$, $120_2$, $120_3$ and $120_4$. MPS 102 processes detected electromagnetic fields to obtain the respective position coordinate readings, which are subsequently stored in database 106. It is recalled that each MPS sensor position coordinate reading is time-tagged, or associated with the exact time at which the reading was obtained. Thus, each MPS data set received from MPS sensor $120_1$ comprises a collection of coordinate readings demonstrating the precise motion trajectory of surgical tool 124 over time.

In procedure 318, cardiac phase information is obtained from cardiac motion. In particular, cardiac phase information is obtained from data streams originating from MPS sensor $120_1$ located on surgical tool 124. Procedure 318 consists of procedures 304, 306, 310, 314 and 316.

In procedure 304, periodic motion frequencies are detected and identified in a time-tagged MPS data set. As surgical tool 124 is guided inside a vessel within the body of a patient, the motion of surgical tool 124 is influenced by two additional factors. The first factor relates to activity of the heart, or cardiac motion, such as systole and diastole. Cardiac motion affects the vessel in a certain way, such as contraction or expansion in varying degrees and at periodic intervals. The second factor relates to breathing activity, or respiratory motion, such as inhaling and exhaling. Respiratory motion affects the vessel in a certain way, such as contraction or expansion in varying degrees and at periodic intervals. Taken together, the overall motion of surgical tool 124 is composed of the cardiac motion and the respiratory motion superimposed onto the basic guiding movement (which corresponds to the vessel topography). The term "organ timing signal" refers herein below to the movement of the blood vessel arising from the periodic motion frequencies (i.e., the cardiac motion and the respiratory motion together).

Since the cardiac motion and respiratory motion are cyclic in nature, the periodic frequencies can be detected in the overall trajectory of surgical tool 124. The specific frequencies relating to the cardiac motion exhibit different characteristics than the specific frequencies relating to the respiratory motion. The specific frequencies relating to the cardiac motion are identified from the detected periodic frequencies. Similarly, the specific frequencies relating to the respiratory motion are identified from the detected periodic frequencies. Processor 108 performs the analysis on the MPS data set and identifies the relevant periodic motion frequencies.

In procedure 306, periodic motion frequencies are filtered from the time-tagged MPS data set. The periodic motion frequencies detected in procedure 304 are separated out from the overall trajectory of surgical tool 124. The remaining motion components correspond to the central axis of the guiding motion of surgical tool 124, which represents the vessel topography, or "centerline trajectory" (referenced procedure 308). The time-tags associated with the MPS data set are retained for each of the filtered periodic motion frequencies. Processor 108 filters out the relevant periodic motion frequencies from the MPS data set.

In procedure 310, the mechanical movement of the vessel originating from the cardiac motion, or "cardiac trajectory", is reconstructed from the MPS data sets and the filtered periodic motion frequencies. In particular, the cardiac trajectory is reconstructed according to the previously identified specific frequencies relating to the cardiac motion. The reconstructed cardiac trajectory may be reflected, for example, by a graph that indicates the trajectory of the vessel due to cardiac motion over a period of time. Processor 108 analyzes the relevant periodic motion frequencies and creates a reconstruction of the cardiac trajectory.

In procedure 312, the mechanical movement of the vessel originating from the respiratory motion, or "respiratory trajectory", is reconstructed from the MPS data sets and the filtered periodic motion frequencies. In particular, the respiratory trajectory is reconstructed according to the previously identified specific frequencies relating to the respiratory motion. The reconstructed respiratory trajectory may be reflected, for example, by a graph that indicates the trajectory of the vessel due to respiratory motion over a period of time. Processor 108 analyzes the relevant periodic motion frequencies and creates a reconstruction of the respiratory trajectory.

Reconstruction of the respiratory trajectory may be based solely on coordinate readings obtained from the external reference sensors (i.e., MPS sensors $120_3$ or $120_4$). It is noted that an additional reference sensor (or plurality thereof) may be attached (i.e., externally or internally) to the body of the patient, to monitor breathing patterns and the like. For example, an intravascular sensor may be used for this purpose. This sensor functions as a confirmation mechanism to provide support data regarding respiratory motion, and more accurately determine periodic motion frequencies relating to respiratory motion. It is noted that the same or additional sensor (or plurality thereof) may be used for gathering additional cardiac data either as a confirmation mechanism and/or for providing supporting data for cardiac phase detection.

In procedure 314, phase detection is performed on the reconstructed cardiac trajectory. The cardiac trajectory consists of different phases or activity-states of the heart, corresponding to different points within a cardiac cycle. The phases repeat themselves periodically with each cycle. The plurality of cardiac activity-states is identified on the reconstructed cardiac trajectory during phase detection. Processor 108 performs the analysis of the cardiac trajectory and identifies the different cardiac cycle phases.

Reference is now made to FIG. 4A, which is a schematic illustration of a sample cardiac trajectory, in electrical signal representation and in mechanical signal representation. The mechanical signal representation of the cardiac trajectory, generally referenced 400, includes a plurality of cardiac activity-states (i.e., cardiac cycle phases), such as activity-states $T_1$, $T_2$ and $T_3$, in each of plurality of cardiac cycles 410, 420 and 430. The mechanical representation of the cardiac trajectory is equivalent to the cardiac trajectory reconstructed from the MPS data sets and the filtered periodic motion frequencies in procedure 310. The electrical signal representation of the cardiac trajectory, generally referenced 450, depicts the same activity-states $T_1$, $T_2$ and $T_3$, in each of plurality of cardiac cycles 410, 420 and 430. However the precise time at which these activity-states occur may be different in the two representations, as there is a slight delay at the electrical representation with respect to the mechanical representation. For example, it is shown that activity-state $T_1$ of cardiac cycle 430 occurs at time $t_A$ in cardiac trajectory 400 and at time $t_B$ in cardiac trajectory 450. Therefore, it is necessary to perform an alignment between the activity states, when using information from the electrical representation for phase detection. The electrical representation of the cardiac trajectory is equivalent to the electrical timing signals obtained by an ECG monitor.

It is noted that the detection of cardiac phases is performed based solely on data sets originating from at least MPS sensor $120_1$ located on surgical tool 124, and perhaps also from the reference sensors (i.e., MPS sensors $120_3$ and $120_4$). These data sets provide a mechanical representation of the cardiac trajectory. No external monitoring device is required to obtain cardiac phase information. It is noted that periodic motion components relating to the respiratory motion may also be used as supporting data for cardiac phase detection. It is further noted that phase detection may be performed on the original MPS data sets, rather than on the reconstructed cardiac trajectory, using the detected and filtered periodic motion frequencies. In this case, the different phases or activity-states of the heart are identified directly on the MPS data sets obtained in procedure 302.

In procedure 316, cardiac phase information is associated with the MPS data sets. Each data set obtained from MPS sensor $120_1$ relating to position of surgical tool 124 is matched to one of plurality of activity-states $T_1$, $T_2$ and $T_3$, according to their corresponding time elements (i.e., time-tags). The position of the inspected vessel, and consequently the position of guided surgical tool 124, is different during different activity-states of the inspected organ. Processor 108 associates between a coordinate reading and the matching phase thereof, and stores the information in database 106.

Respiratory phase information may be obtained from the respiratory motion, in a similar manner as cardiac phase information is obtained from the cardiac motion. Respiration activity-states may be identified on the reconstructed respiratory trajectory using the periodic motion components relating to the respiratory motion. Periodic motion components relating to the respiratory motion may also be used in correlation of non-corresponding data sets (discussed with reference to FIG. 8).

Respiratory phase information is obtained from respiratory motion in optional procedure 320. Procedure 320 consists of procedures 304, 306, 312, 322 and 324. In procedure 312, the respiratory trajectory is reconstructed from the MPS data sets and the filtered periodic motion frequencies, as elaborated upon earlier. In procedure 322, phase detection is performed on the reconstructed respiratory trajectory. Similar to the cardiac trajectory, the respiratory trajectory consists of different phases or activity-states of the lungs, corresponding to different points within a respiratory cycle. The respiratory activity-states of the lungs may be identified from the phases of the respiratory trajectory. The phases repeat themselves periodically with each cycle. The plurality of respiratory activity-states is identified on the reconstructed respiratory trajectory during phase detection. Processor 108 performs the analysis of the respiratory trajectory and identifies the different respiratory cycle phases.

Reference is now made to FIG. 4B, which is a schematic illustration of a sample respiratory trajectory in mechanical signal representation. The mechanical signal representation of the respiratory trajectory, generally referenced 460, includes a plurality of respiratory activity-states (i.e., respiratory cycle phases), such as activity-states $T_4$, $T_5$ and $T_6$. The mechanical representation of the respiratory trajectory is equivalent to the respiratory trajectory reconstructed from the MPS data sets and the filtered periodic motion frequencies in procedure 310.

It is noted that the detection of respiratory phases is performed based solely on data sets originating from MPS sensor $120_1$ located on surgical tool 124, and from MPS sensors $120_3$ and $120_4$, located on a selected area of patient body 130, and a known area on the surface on which the patient rests, respectively. These data sets provide a mechanical representation of the respiratory trajectory. No external monitoring device is required to obtain respiratory phase information. It is further noted that phase detection may be performed on the original MPS data sets, rather than on the reconstructed respiratory trajectory, using the detected and filtered periodic motion frequencies. In this case, the different phases or activity-states of the lung are identified directly on the MPS data sets obtained in procedure 302.

It is noted that the actual value of the cardiac rate or respiratory rate of the patient may be obtained without the use of an external monitoring device (such as an ECG device). The cardiac rate or respiratory rate of the patient may be obtained solely from MPS sensors $120_1$, $120_3$ and $120_4$, either individually or jointly.

In procedure 324, respiratory phase information is associated with the MPS data sets. Each data set obtained from MPS sensor $120_1$ relating to position of surgical tool 124 is matched to one of plurality of activity-states $T_4$, $T_5$ and $T_6$, according to their corresponding time tags. Procedure 324 is analogous to procedure 316 discussed above.

Figure 5:
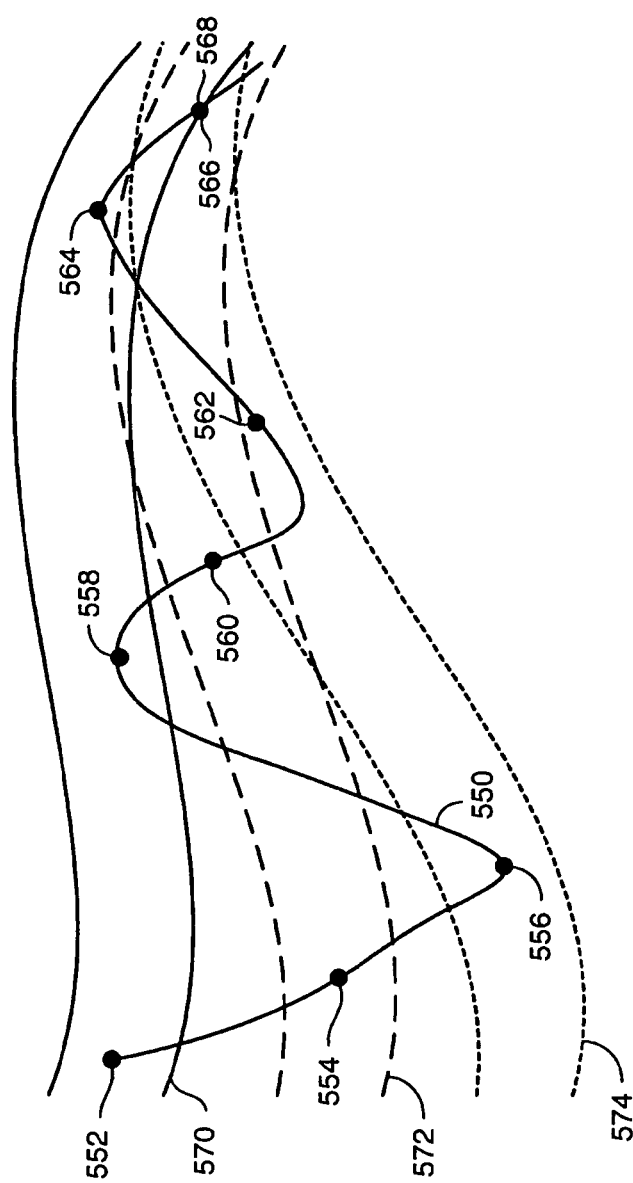
FIG. 5 is a schematic illustration of a trajectory of the surgical tool of the system of FIG. 1, inside a vessel in the body of a patient, respective of different activity-states of the cardiac trajectory of FIG. 4.

Reference is now made to FIG. 5, which is a schematic illustration of a trajectory of the surgical tool of the system of FIG. 1, inside a vessel in the body of a patient, respective of different activity-states of the cardiac trajectory of FIG. 4. At activity-state $T_1$ of each of the cardiac cycles 410, 420 and 430, the position of the vessel is represented by a vessel image 570 (indicated in FIG. 5 with solid lines). At activity-state $T_2$ of each of the cardiac cycles 410, 420 and 430, the position of the vessel is represented by a vessel image 572 (indicated in FIG. 5 with dashed lines). At activity-state $T_3$ of each of the cardiac cycles 410, 420 and 430, the position of the vessel is represented by a vessel image 574 (indicated in FIG. 5 with dotted lines). Thus, each of the coordinates 552, 554, 556, 558, 560, 562, 564, 566 and 568 corresponds to a position of surgical tool 124, while the vessel is at a different position, in a different activity-state of a cardiac cycle.

For example, coordinate 552 corresponds to activity-state $T_1$ in cardiac cycle 410, meaning that when MPS sensor $120_1$ on surgical tool 124 is at coordinate 552, the heart of the patient is at activity-state $T_1$. Coordinate 554 corresponds to activity-state $T_2$ in cardiac cycle 410, meaning that when MPS sensor $120_1$ on surgical tool 124 is at coordinate 554, the heart of the patient is at activity-state $T_2$. Coordinate 556 corresponds to activity-state $T_3$ in cardiac cycle 410, meaning that when MPS sensor $120_1$ on surgical tool 124 is at coordinate 556, the heart of the patient is at activity-state $T_3$. Coordinate 558 corresponds to activity-state $T_1$ in cardiac cycle 420. Coordinate 560 corresponds to activity-state $T_2$ in cardiac cycle 420. Coordinate 562 corresponds to activity-state $T_3$ in cardiac cycle 420. Coordinate 564 corresponds to activity-state $T_1$ in cardiac cycle 430. Coordinate 566 corresponds to activity-state $T_2$ in cardiac cycle 430. Coordinate 568 corresponds to activity-state $T_3$ in cardiac cycle 430. It is noted that coordinates 552, 554, 556, 558, 560, 562, 564, 566 and 568 are related to the respiratory activity states $T_4$, $T_5$, $T_6$ in a similar manner.

According to another aspect of the disclosed technique, position measurements, together with acquired images, are processed with respect to the activity-state of the inspected organ at the time of acquisition or measurement. For example, with reference to FIG. 1, display 110 displays the trajectory of a surgical tool 124 superimposed on a two-dimensional image of an inspected organ, wherein the two-dimensional image corresponds to an activity-state determined by the current position of surgical tool 124 inside the inspected organ. The system records the path which surgical tool 124 follows inside the inspected organ, in either a forward or a backward direction. The system further registers this path with monitored activity-states of the inspected organ and with the instantaneous position of surgical tool 124.

Figure 6:
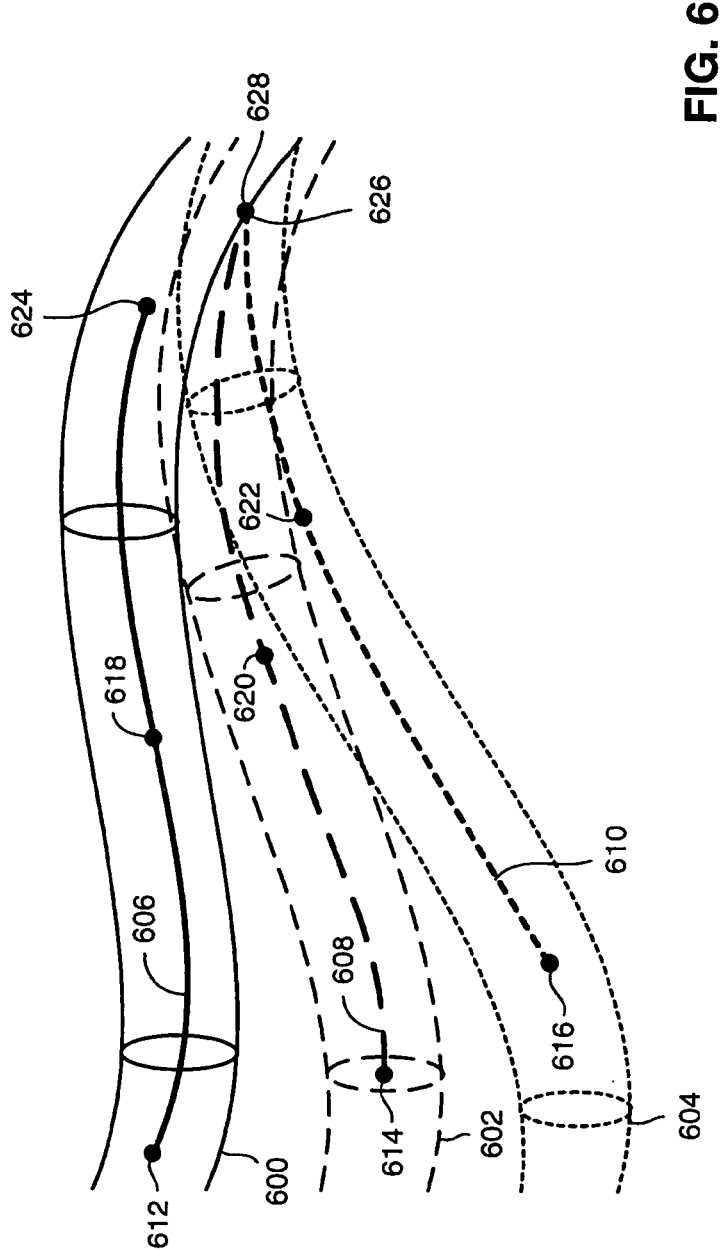
FIG. 6 is a schematic illustration of trajectories of a guided surgical tool inside a vessel in the body of a patient, each trajectory processed with respect to a different activity-state.

Reference is now made to FIG. 6, which is a schematic illustration of trajectories of a guided surgical tool inside a vessel in the body of a patient, each trajectory processed with respect to a different activity-state. For example, processor 108 associates for a given two-dimensional image acquired during activity-state $T_1$, all the position coordinate readings of surgical tool 124 (i.e., coordinates 612, 618 and 624) which were detected during activity-state $T_1$ at any cycle of cardiac trajectory 400. Similarly, processor 108 associates for a given two-dimensional image acquired during activity-state $T_2$, all the position coordinate readings (i.e., coordinates 614, 620 and 626) which were detected during activity-state $T_2$ at any cycle of cardiac trajectory 400; and further associates for a given two-dimensional image acquired during activity-state $T_3$, all the position coordinate readings (i.e., coordinates 616, 622 and 628) which were detected during activity-state $T_3$ at any cycle of cardiac trajectory 400.

Processor 108 calculates a trajectory 606 from points 612, 618 and 624, associated with activity state $T_1$. Similarly, processor 108 calculates a trajectory 608 from points 614, 620 and 626 associated with activity state $T_2$, and further calculates a trajectory 610 from points 616, 622 and 628 associated with activity state $T_3$.

Processor 108 associates between each of the calculated trajectories and a two-dimensional image, respective of a given organ activity-state. Processor 108 associates between trajectory 612 and two-dimensional image 600 (indicated with solid lines), respective of activity state $T_1$. Similarly, processor 108 associates between trajectory 614 and two-dimensional image 602 (indicated with dashed lines), respective of activity state $T_2$ and further between trajectory 614 and two-dimensional image 604 (indicated with dotted lines), respective of activity state $T_3$.

Display 110 presents a superimposition of each of the calculated trajectories on its respective two-dimensional image. For example, display 110 presents trajectory 606 superimposed on two-dimensional image 600, trajectory 608 superimposed on two-dimensional image 602 and trajectory 610 superimposed on two-dimensional image 604. Display 110 may present these images as a single image frame shown one at a time, or a sequence of images (i.e., motion picture) shown consecutively.

It is noted that points 612, 614, 616, 618, 620, 622, 624, 626 and 628 represent a situation similar to that presented by points 552, 554, 556, 558, 560, 562 564, 566 and 568 with respect to FIG. 5. However, according to an aspect of the disclosed technique presented in FIG. 6, processor 108 calculates a trajectory of surgical tool 124 based on the position coordinate readings detected during a given activity-state. Thus, each trajectory corresponds to a different activity-state of the inspected organ. Processor 108 further associates each calculated trajectory with a vessel image acquired during the corresponding activity-state.

Figure 7:
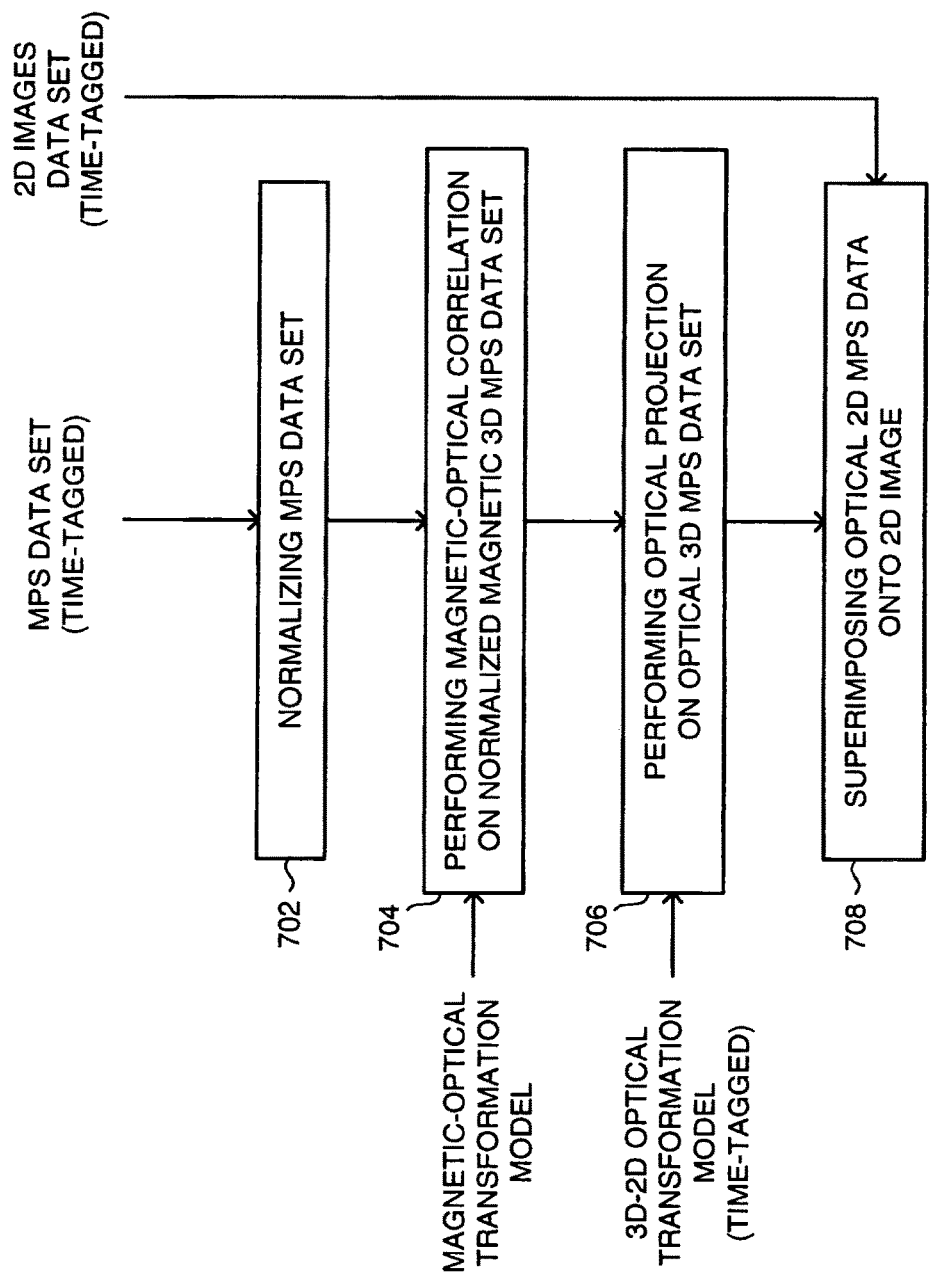
FIG. 7 is a block diagram of a method for superimposing MPS data onto two-dimensional image data for corresponding data sets, operative in accordance with another embodiment of the disclosed technique.

Reference is now made to FIG. 7, which is a block diagram of a method for superimposing MPS data onto two-dimensional image data for corresponding data sets, operative in accordance with another embodiment of the disclosed technique. It is recalled that the position coordinate readings obtained from MPS 102 is time-tagged. Similarly, the sequence of two-dimensional images obtained from medical imaging device 104 is time-tagged. "Corresponding data sets" refer to a pair of data sets which have the same time-tags. It is noted that the time-tag of a data set refers to the set of time-tags of the elements within the data set. For example, an MPS data set is corresponding with a two-dimensional images data set if readings in the MPS data set have the same time-tag as images in the two-dimensional images data set. Corresponding data sets represent data sets that occur during the same session in a medical procedure. "Non-corresponding data sets" refer to a pair of data sets which have different time-tags. For example, an MPS data set is non-corresponding with a two-dimensional images data set if readings in the MPS data set have a different time-tag than all the images in the two-dimensional images data set. Non-corresponding data sets represent data sets that were recorded during different sessions (within the same or different medical procedures).

In procedure 702, an MPS data set is normalized. The MPS data set, which comprises three-dimensional coordinate readings in the magnetic coordinate system, is obtained from MPS 102. Normalization compensates for patient movement or movement of medical imaging device 116, as discussed with reference to FIG. 1. Normalization is performed using MPS data with corresponding time-tags from the reference sensors (i.e., MPS sensors $120_3$ or $120_4$), and perhaps also MPS sensor $120_2$ as well.

In procedure 704, magnetic-optical correlation is performed on the normalized MPS data set. The correlation procedure transforms the three-dimensional position magnetic coordinate into a three-dimensional coordinate in the optical coordinate system. The correlation procedure is based on the magnetic-optical transformation model, determined in procedure 210 with reference to FIG. 2.

In procedure 706, optical projection is performed on the correlated MPS data set. The optical projection procedure transforms the three-dimensional position MPS coordinate reading in the optical coordinate system to a two-dimensional coordinate. The optical projection procedure is based on the three-dimensional to two-dimensional optical transformation model, determined in procedure 228 with reference to FIG. 2. It is noted that the three-dimensional to two-dimensional optical transformation model is a function of certain parameters (i.e., internal and external optical parameters and image distortion parameters of medical imaging device 104), which are computed at a given instant in time, and as such, is time-tagged. Therefore the optical projection procedure is based on a three-dimensional to two-dimensional optical transformation model which has the same time-tag as the MPS data set.

A direct transformation between 3D MPS data to 2D image coordinates can be used in case such a direct translation was computed. Compensation for optical distortions is done at a given instant in time and as such, is time-tagged.

In procedure 708, the MPS data set is superimposed onto an image from the two-dimensional images data set. The two-dimensional images data set is obtained from medical imaging device 104. The MPS data set now includes two-dimensional position coordinates in the optical coordinate system. With reference to FIG. 1, processor 108 associates between a position coordinate reading and a two-dimensional image, in accordance with their mutual time-tag. Display 110 may present a picture showing the position of surgical tool 124 respective of the inspected organ, at a given point in time, in accordance with acquired two-dimensional image data and acquired MPS data. Further, as will be elaborated upon with reference to FIGS. 9 and 10, display 110 may present a motion picture showing the trajectory of the guided surgical tool respective of the inspected organ, in accordance with acquired two-dimensional image data set and acquired MPS data set.

The MPS data and two-dimensional image data may further be associated with activity state information. With reference to FIG. 1, processor 108 associates between a position coordinate reading and a two-dimensional image, in accordance with their mutual time-tag, respective of a given organ activity-state. Display 110 may present an image frame showing the position of surgical tool 124, respective of the inspected organ at a given activity-state, in accordance with acquired two-dimensional image data, acquired MPS data, and associated activity-state information. Further, display 110 may present a motion picture showing the trajectory of the guided surgical tool respective of the inspected organ at a given activity-state, in accordance with acquired two-dimensional image data set, acquired MPS data set, and associated activity-state information. This will be elaborated upon with reference to FIGS. 9 and 10.

Figure 8:
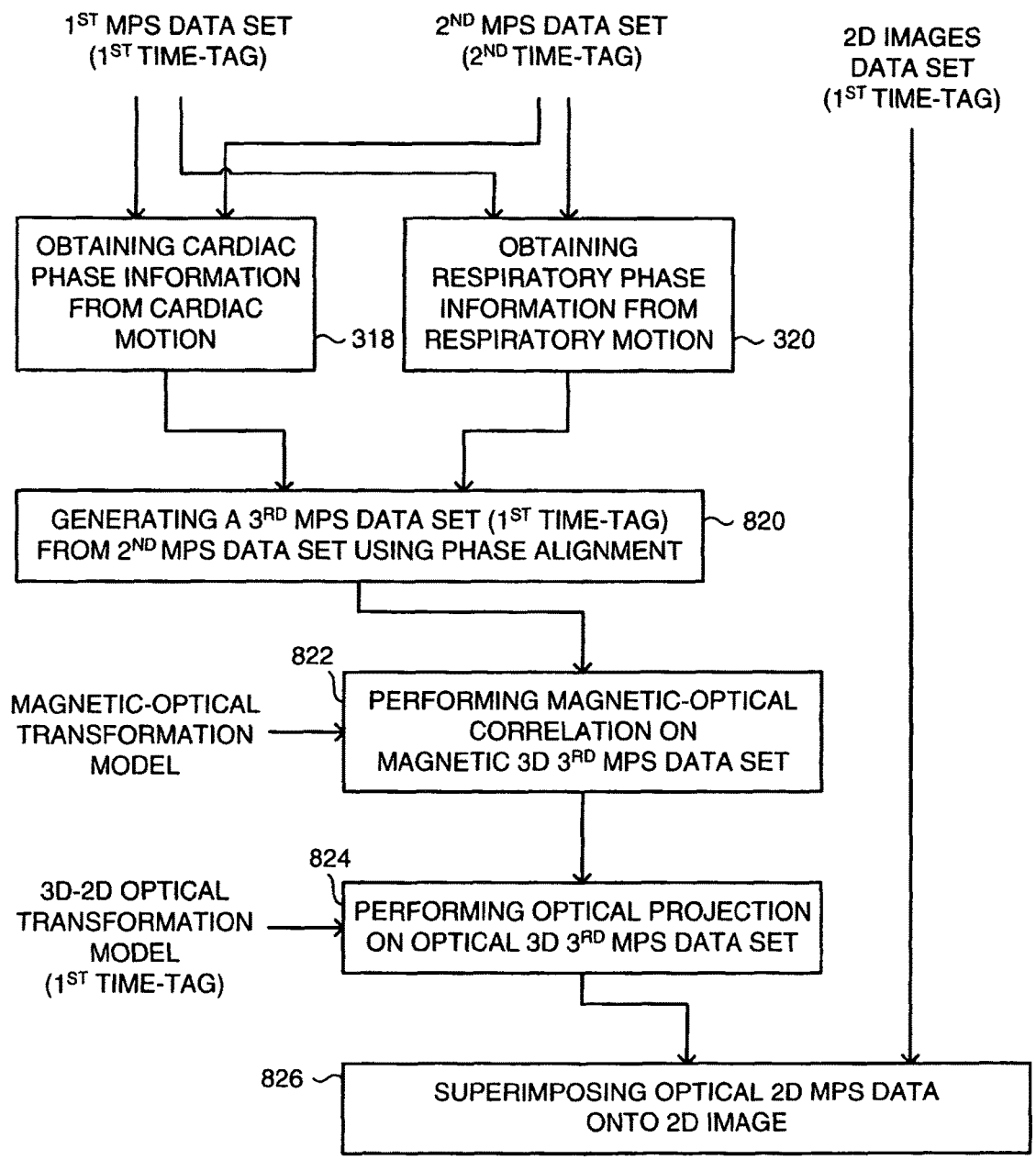
FIG. 8 is a block diagram of a method for superimposing MPS data onto two-dimensional image data for non-corresponding data sets, operative in accordance with a further embodiment of the disclosed technique.

Reference is now made to FIG. 8, which is a block diagram of a method for superimposing MPS data onto two-dimensional image data for non-corresponding data sets, operative in accordance with a further embodiment of the disclosed technique. A first MPS data set with a first time-tag is corresponding with a two-dimensional images data set. A second MPS data set with a second time-tag is non-corresponding with the two-dimensional images data set. The time-tagged MPS data sets are obtained from MPS 102. The time-tagged two-dimensional images data set is obtained from medical imaging device 104.

In procedure 318, cardiac phase information is obtained from cardiac motion data, for both the first MPS data set and the second MPS data set. Procedure 318 involves detecting and identifying periodic motion frequencies, filtering periodic motion components, reconstructing the cardiac trajectory from the MPS data set and filtered periodic motion frequencies, performing phase detection on the reconstructed cardiac trajectory, and associating each coordinate reading in the MPS data set with a cardiac phase, in accordance with their time-tags. Periodic motion components relating to the respiratory motion may also be used as supporting data for cardiac phase detection. Procedure 318 is described in detail with respect to FIG. 3.

In procedure 320, respiratory phase information is obtained from respiratory motion data, for both the first MPS data set and the second MPS data set. It is noted that procedure 320 is optional, and may be performed instead of procedure 318, or in conjunction with procedure 318. Procedure 320 involves detecting and identifying periodic motion frequencies, filtering periodic motion components, reconstructing the respiratory trajectory from the MPS data set and filtered periodic motion frequencies, performing phase detection on the reconstructed respiratory trajectory, and associating each coordinate reading in the MPS data set with a respiratory phase, in accordance with their time-tags. Procedure 320 is described in detail with respect to FIG. 3.

In procedure 820, a third MPS data set with the same time-tag as the first MPS data set is generated from the second MPS data set, using phase alignment between the phases of the two MPS data sets. In particular, the coordinate readings of the second MPS data set are assigned the same time-tags as the coordinate readings of the first MPS data set, by matching the phases of the coordinate readings from each data set. Each of the detected phases in the second MPS data set is mapped to the matching phase in the first MPS data set. Each of the detected phases in the second MPS data set (and thus each coordinate reading associated with that phase) is then assigned a new time-tag based on the time-tag of the matching phase in the first MPS data set. For example, if phase A occurs at time "x" in the second MPS data set, and phase A occurs at time "y" in the first MPS data set, then phase A is reassigned time-tag "y" in the third MPS data set. The phase mapping aligns the phases of the cardiac trajectory of the second data set with the cardiac trajectory of the first MPS data set. After the procedures of mapping and reassigning have been completed, the resulting data set will have the same time-tag as the first MPS data set, and hence as the two-dimensional image data set. Therefore, the third MPS data set will be corresponding with the two-dimensional image data set. It is noted that periodic motion components relating to the respiratory motion may be used in addition to, or instead of, the periodic motion components relating to the cardiac motion, for performing phase alignment. It is noted that procedure 820 may generate simply an index of each element in the third data set.

In procedure 822, magnetic-optical correlation is performed on the third MPS data set. It is noted that normalization, or compensating for patient movement or movement of medical imaging device 116, is performed prior to procedure 822. Normalization is discussed in procedure 702 with reference to FIG. 7. Normalization may be performed immediately prior to procedure 820 or immediately after procedure 820. The correlation procedure transforms the three-dimensional position magnetic coordinate into a three-dimensional coordinate in the optical coordinate system. The correlation procedure is based on the magnetic-optical transformation model, determined in procedure 210 with reference to FIG. 2.

In procedure 824, optical projection is performed on the correlated third MPS data set. The optical projection procedure transforms the three-dimensional position MPS coordinate in the optical coordinate system to a two-dimensional optical coordinate. The optical projection procedure is based on the three-dimensional to two-dimensional optical transformation model, determined in procedure 228 with reference to FIG. 2. It is recalled that the three-dimensional to two-dimensional optical transformation model is time-tagged. Therefore the optical projection procedure is based on a three-dimensional to two-dimensional optical transformation model which has the same time-tag as first MPS data set.

In procedure 826, the third MPS data set is superimposed onto an image from the two-dimensional images data set. With reference to FIG. 1, processor 108 associates between a position coordinate reading in the third MPS data set and a two-dimensional image, in accordance with their mutual time-tag. Display 110 may present an image frame showing the position of surgical tool 124 respective of the inspected organ, at a given point in time, in accordance with acquired two-dimensional image data and acquired MPS data. Further, display 110 may present a motion picture showing the trajectory of the guided surgical tool respective of the inspected organ, in accordance with acquired two-dimensional image data set and acquired MPS data set. The MPS data and two-dimensional image data may further be associated with activity state information. Display 110 may further simultaneously present MPS data with a corresponding data set and with a non-corresponding data set. For example, presenting a superimposition of current real-time MPS data on current real-time images (i.e., corresponding data sets), while at the same time presenting a superimposition of the same current real-time MPS data on previously taken images (i.e., non-corresponding data sets) using associated activity state information.

Figure 9:
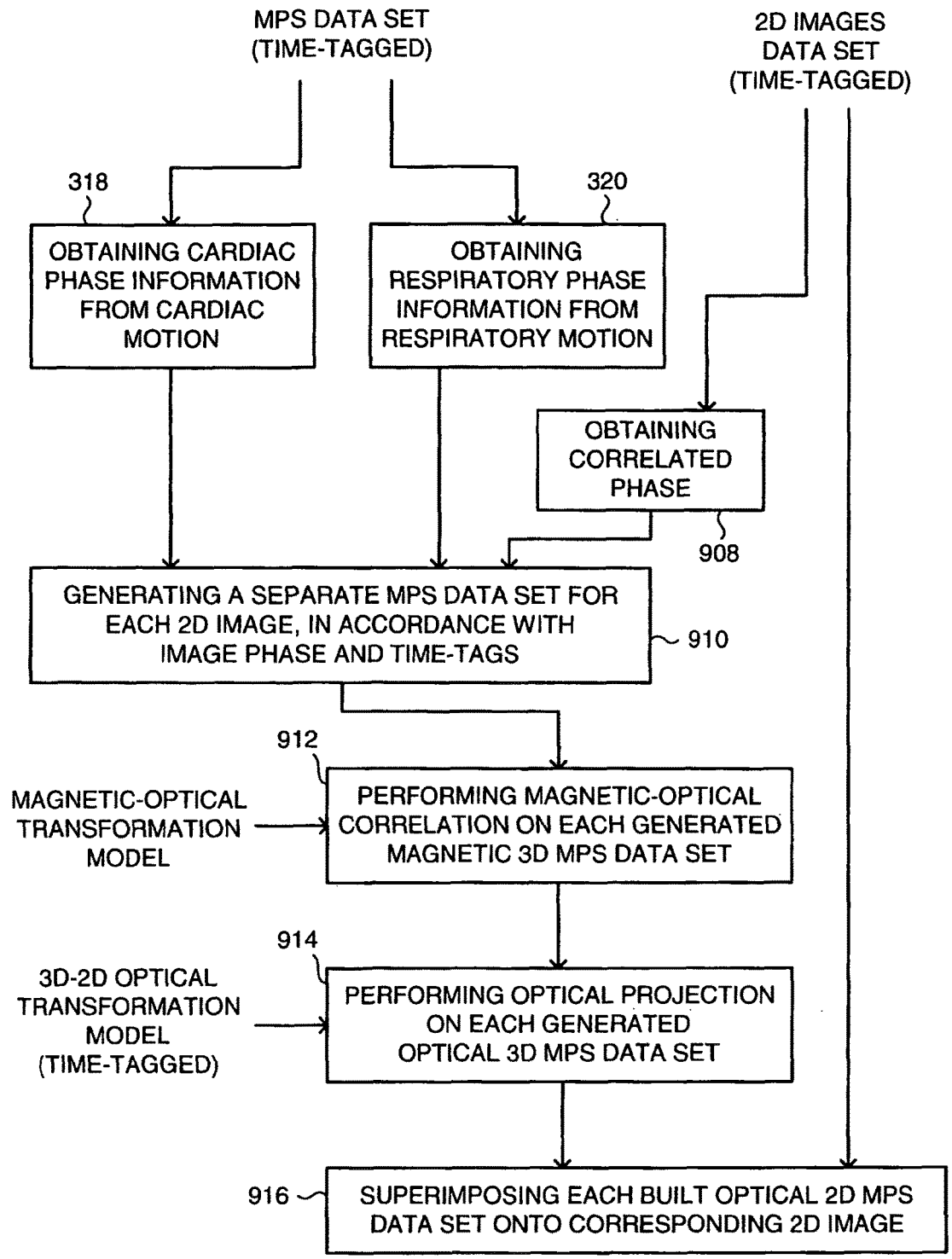
FIG. 9 is a block diagram of a method for constructing trajectories of a guided surgical tool within the body of a patient, respective of different activity-states of an inspected organ, operative in accordance with another embodiment of the disclosed technique.

Reference is now made to FIG. 9, which is a block diagram of a method for constructing trajectories of a guided surgical tool within the body of a patient, respective of different activity-states of an inspected organ (e.g., such as shown in FIG. 6), operative in accordance with another embodiment of the disclosed technique. In the following example, an MPS data set corresponding with a two-dimensional image data set is used. It is noted that non-corresponding data sets may be used as well, after simply undergoing phase alignment, similar to procedure 820 discussed with reference to FIG. 8. The time-tagged MPS data set is obtained from MPS 102. The time-tagged two-dimensional images data set is obtained from medical imaging device 104.

In procedure 318, cardiac phase information is obtained from cardiac motion data, for the MPS data set. Procedure 318 involves detecting and identifying periodic motion frequencies, filtering periodic motion components, reconstructing the cardiac trajectory from the MPS data set and filtered periodic motion frequencies, performing phase detection on the reconstructed cardiac trajectory, and associating each coordinate reading in the MPS data set with a phase, in accordance with their time-tags. Periodic motion components relating to the respiratory motion may also be used as supporting data for cardiac phase detection. Procedure 318 is described in detail with respect to FIG. 3.

In procedure 320, respiratory phase information is obtained from respiratory motion data, for both the first MPS data set and the second MPS data set. It is noted that procedure 320 is optional, and may be performed instead of procedure 318, or in conjunction with procedure 318. Procedure 320 involves detecting and identifying periodic motion frequencies, filtering periodic motion components, reconstructing the respiratory trajectory from the MPS data set and filtered periodic motion frequencies, performing phase detection on the reconstructed respiratory trajectory, and associating each coordinate reading in the MPS data set with a respiratory phase, in accordance with their time-tags. Procedure 320 is described in detail with respect to FIG. 3.

In procedure 908, correlated phase information is obtained for the two-dimensional images data set. The phase information is correlated in the sense that the phase information is not obtained directly from the images but from correlated MPS data (occurring at the same time as a given image). The phases or activity-states of the heart, such as activity-states $T_1$, $T_2$ and $T_3$ with reference to FIG. 4, during which each two-dimensional image was acquired, is identified. Identification of the activity-states makes use of the time-tags taken during acquisition of all the images, and the phases of an MPS data set having the same time-tags.

A monitoring device such as an ECG may be used in conjunction with MPS data to obtain phase information of the two-dimensional image data set in certain instances. For example, if there was no sensor within the body of the patient during acquisition of a given image (e.g., during the very beginning of the medical procedure when medical images are taken before the guide wire is inserted into the vessel), information from the monitoring device may be used together with non-corresponding MPS data. In such a case, phase alignment is performed between the mechanical representation based phase data obtained by the MPS data and the external phase obtained by the monitoring device (such as electrical representation based phase data obtained from an ECG device). Phase alignment between the mechanical and electrical based data is necessary in order to account for different latencies originating from the different sampled signals that represent the same cardiac trajectory. It is noted that data obtained from the monitoring device is also time-tagged.

In procedure 910, a separate MPS data set is generated for each two-dimensional image, in accordance with the image phase and time-tags. All the MPS position coordinate readings acquired during the same phase are combined into a single data set. After procedure 910 has been completed, every image of the two-dimensional image data set has a corresponding MPS data set containing therein only those coordinate readings which were acquired in the same phase as that image.

In procedure 912, magnetic-optical correlation is performed on each MPS data set generated in procedure 910. It is noted that normalization, or compensating for patient movement or movement of medical imaging device 116, is performed prior to procedure 912. Normalization is discussed in procedure 702 with reference to FIG. 7. Normalization may be performed immediately prior to procedure 910 or immediately after procedure 910. The correlation procedure transforms the three-dimensional position magnetic coordinate into a three-dimensional coordinate in the optical coordinate system. The correlation procedure is based on the magnetic-optical transformation model, determined in procedure 210 with reference to FIG. 2.

In procedure 914, optical projection is performed on each correlated MPS data set generated in procedure 910. The optical projection procedure transforms the three-dimensional position MPS coordinate in the optical coordinate system to a two-dimensional optical coordinate. The optical projection procedure is based on the three-dimensional to two-dimensional optical transformation model, determined in procedure 228 with reference to FIG. 2. It is recalled that the three-dimensional to two-dimensional optical transformation model is time-tagged. Therefore the optical projection procedure is based on a three-dimensional to two-dimensional optical transformation which has the same time-tag as the MPS data set.

In procedure 916, each MPS data set generated in procedure 910 is superimposed onto the corresponding two-dimensional image. For each two-dimensional image, the MPS coordinate readings which were acquired during the same phase at the two-dimensional image are superimposed onto that image. The coordinate readings are then connected together by lines, thereby composing a spline representing the trajectory of surgical tool 124 respective of an activity state of the inspected organ. Display 110 may present an image frame showing the position of surgical tool 124 respective of the inspected organ, at a given point in time, in accordance with acquired two-dimensional image data and acquired MPS data. Further, display 110 may present a motion picture showing the trajectory of the guided surgical tool respective of the inspected organ, in accordance with acquired two-dimensional image data set and acquired MPS data set. The MPS data and two-dimensional image data may further be associated with activity state information. Display 110 may further simultaneously present a superimposition of current real-time MPS data on current real-time images, while presenting a superimposition of the same current real-time MPS data on previously taken images, using associated activity state information.

Figure 10:
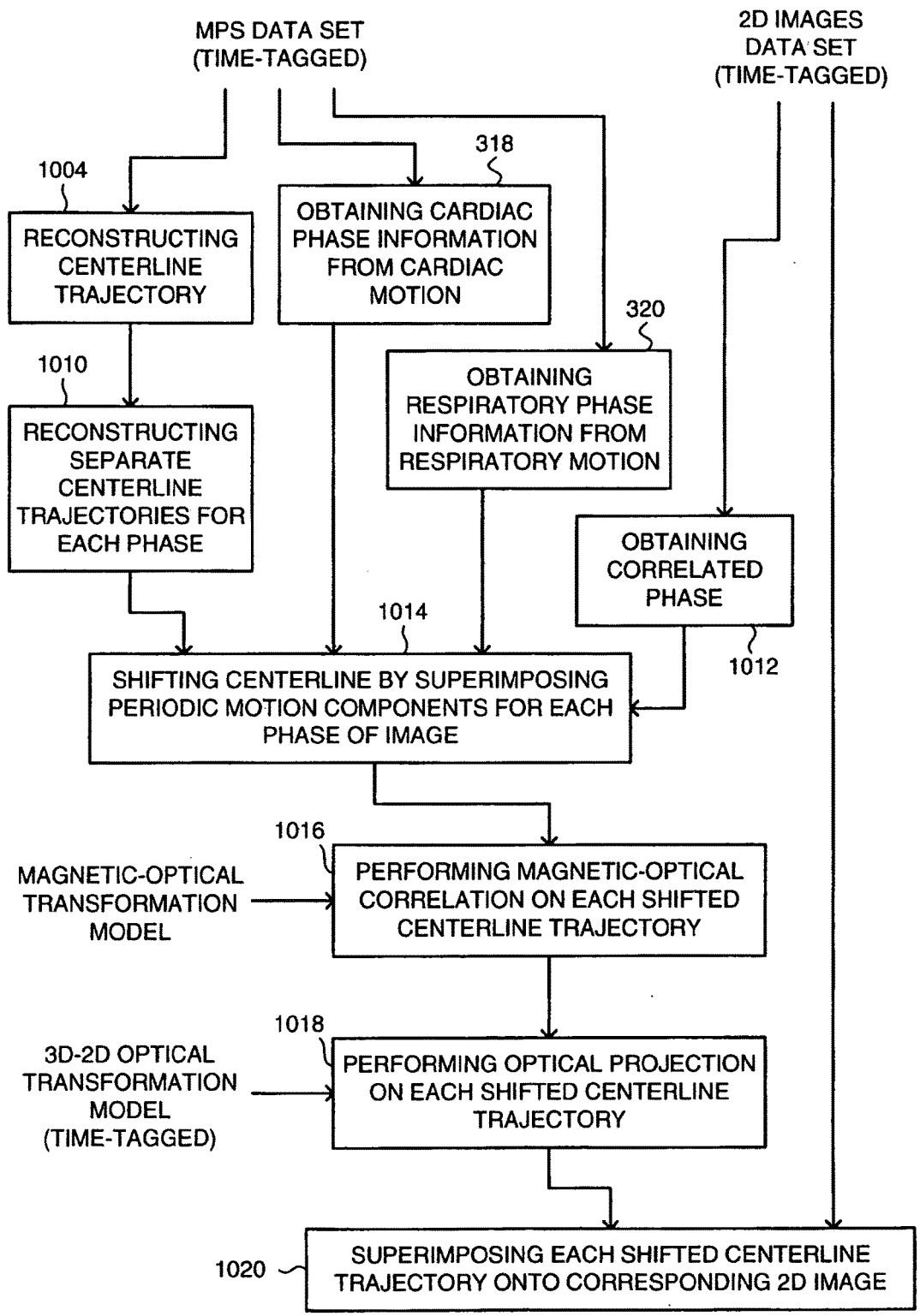
FIG. 10 is a block diagram of an additional method for constructing trajectories of a guided surgical tool within the body of a patient, respective of different activity-states of an inspected organ, operative in accordance with a further embodiment of the disclosed technique.

Reference is now made to FIG. 10, which is a block diagram of an additional method for constructing trajectories of a guided surgical tool within the body of a patient, respective of different activity-states of an inspected organ, operative in accordance with a further embodiment of the disclosed technique. In the following example, an MPS data set corresponding with a two-dimensional image data set is used. It is noted that non-corresponding data sets may be used as well, after simply undergoing phase alignment, similar to the procedure discussed with reference to FIG. 8. A time-tagged MPS data set is obtained from MPS 102. A time-tagged two-dimensional images data set is obtained from medical imaging device 104.

In procedure 318, cardiac phase information is obtained from cardiac motion data, for the MPS data set. Procedure 318 involves detecting and identifying periodic motion frequencies, filtering periodic motion components, reconstructing the cardiac trajectory from the MPS data set and filtered periodic motion frequencies, performing phase detection on the reconstructed cardiac trajectory, and associating each coordinate reading in the MPS data set with a phase, in accordance with their time-tags. Periodic motion components relating to the respiratory motion may also be used as supporting data for cardiac phase detection. Procedure 318 is described in detail with respect to FIG. 3.

In procedure 320, respiratory phase information is obtained from respiratory motion data, for both the first MPS data set and the second MPS data set. It is noted that procedure 320 is optional, and may be performed instead of procedure 318, or in conjunction with procedure 318. Procedure 320 involves detecting and identifying periodic motion frequencies, filtering periodic motion components, reconstructing the respiratory trajectory from the MPS data set and filtered periodic motion frequencies, performing phase detection on the reconstructed respiratory trajectory, and associating each coordinate reading in the MPS data set with a respiratory phase, in accordance with their time-tags. Procedure 320 is described in detail with respect to FIG. 3.

In procedure 1004, the centerline trajectory is reconstructed. After the periodic motion components are separated out from the overall trajectory of surgical tool 124, the remaining motion components corresponds to the central axis of the guiding motion of surgical tool 124, or centerline trajectory. Procedure 1004 is similar to procedure 308 with reference to FIG. 3.

In procedure 1010, separate centerline trajectories are reconstructed for each phase. Based on the time-tags and the detected phases of the cardiac trajectory, the centerline positions are matched according to phase, and a different trajectory is built for each phase.

In procedure 1012, correlated phase information is obtained for the two-dimensional images data set. The phase is correlated in the sense that the phase information is not obtained directly from the images but from correlated MPS information (occurring at the same time as a given image). The phases or activity-states of the heart, such as activity-states $T_1$, $T_2$ and $T_3$, with reference to FIG. 4, during which each two-dimensional image was acquired, is identified. Identification of the activity-states makes use of the time-tags taken during acquisition of all the images, and the phases of an MPS data set having the same time-tags. A monitoring device such as an ECG may be used in conjunction with MPS data to obtain phase information of the two-dimensional image data set in certain instances, as discussed with reference to FIG. 9. In such a case, phase alignment is done between the mechanical based phase data and the electrical based phase data in order to account for different latencies originating from the different sampled signals that represent the same cardiac trajectory. Procedure 1012 is similar to procedure 908 with reference to FIG. 9.

In procedure 1014, each centerline trajectory is shifted by superimposing the matching periodic motion components, for each phase of the images in two-dimensional images data set. The periodic motion components, relating to cardiac motion and respiratory motion, are added on to the centerline trajectories. For each separate centerline trajectory, respective of a given phase, the periodic motion components of that phase are added onto the centerline trajectory. Each centerline trajectory is then shifted, in accordance with the added periodic motion components.

In procedure 1016, magnetic-optical correlation is performed on each cardiac trajectory shifted in procedure 1014. It is noted that normalization, or compensating for patient movement or movement of medical imaging device 116, is performed prior to procedure 1016. Normalization is discussed in procedure 702 with reference to FIG. 7. Normalization may be performed immediately prior to procedure 1014 or immediately after procedure 1014. The correlation procedure transforms the three-dimensional position magnetic coordinate into a three-dimensional coordinate in the optical coordinate system. The correlation procedure is based on the magnetic-optical transformation model, determined in procedure 210 with reference to FIG. 2.

In procedure 1018, optical projection is performed on each correlated cardiac trajectory shifted in procedure 1014. The optical projection procedure transforms the three-dimensional position MPS coordinate in the optical coordinate system to a two-dimensional optical coordinate. The optical projection procedure is based on the three-dimensional to two-dimensional optical transformation model, determined in procedure 228 with reference to FIG. 2. It is recalled that the three-dimensional to two-dimensional optical transformation model is time-tagged. Therefore the optical projection procedure is based on a three-dimensional to two-dimensional optical transformation which has the same time-tag as the cardiac trajectory.

In procedure 1020, each shifted centerline trajectory is superimposed onto the corresponding two-dimensional image. For each two-dimensional image, the MPS coordinate readings of the centerline trajectory matching the same phase at the two-dimensional image are superimposed onto that image. The coordinate readings are then connected together by lines, thereby composing a spline representing the trajectory of surgical tool 124 respective of an activity state of the inspected organ. Display 110 may present an image frame showing the position of surgical tool 124 respective of the inspected organ, at a given point in time, in accordance with acquired two-dimensional image data and acquired MPS data. Further, display 110 may present a motion picture showing the trajectory of the guided surgical tool respective of the inspected organ, in accordance with acquired two-dimensional image data set and acquired MPS data set. The MPS data and two-dimensional image data may further be associated with activity state information. Display 110 may further simultaneously present a superimposition of current real-time MPS data on current real-time images, while presenting a superimposition of the same current real-time MPS data on previously taken images, using associated activity state information.

It will be appreciated by persons skilled in the art that the disclosed technique is not limited to what has been particularly shown and described hereinabove. Rather the scope of the disclosed technique is defined only by the claims, which follow.

The invention claimed is:

1. An apparatus for generating an organ timing signal relating to an organ within a body of a patient, said apparatus comprising:
   a medical positioning system (MPS) including an electromagnetic sensor configured to be attached to an external area of the patient body, said MPS being configured to determine a three-dimensional position of said sensor and thereby the external area of the patient body by processing transmitted electromagnetic signals transmitted by the MPS with detected electromagnetic signals detected by the sensor, said MPS further generating time-tagged MPS data sets, each of said MPS data sets comprising a collection of three-dimensional position coordinate readings wherein each of the readings is associated with a respective time at which the reading was obtained, said readings demonstrating the overall motion trajectory of said sensor over time; and
   a processor coupled with said MPS, generating said organ timing signal from said MPS data sets by detecting and identifying periodic motion frequencies in said time-tagged MPS data sets, and filtering said periodic motion frequencies from said MPS data sets so as to separate out said periodic motion frequencies corresponding to said organ timing signal from said overall motion trajectory of said sensor.

2. The apparatus according to claim 1 wherein said MPS determines the three-dimensional position of said sensor with respect to a reference location.

3. The apparatus according to claim 2 wherein said reference location is stationary with respect to said body of the patient.

4. The apparatus according to claim 1 wherein said three-dimensional position of said sensor is for movement compensation.

5. The apparatus according to claim 1, further comprising at least one additional electromagnetic sensor attached to a known area on the surface on which said patient rests, said electromagnetic sensor obtaining three-dimensional position information of said area, for compensating for movement of said patient.

6. The apparatus according to claim 1, wherein said processor reconstructs a respiratory trajectory from said MPS data sets and said filtered periodic motion frequencies, said respiratory trajectory representing a mechanical movement of said patient originating from respiratory motion.

7. The apparatus according to claim 6, wherein said processor detects phase information of said organ by identifying a plurality of phases on said reconstructed respiratory trajectory.

8. The apparatus according to claim 7, wherein said organ is a lung.

9. The apparatus according to claim 7, wherein said sensor is a first sensor and wherein said time-tagged MPS data sets are first time-tagged MPS data sets; and
   said MPS being configured to determine a three-dimensional position of a second electromagnetic sensor attached to a surgical tool configured to be inserted in the body of the patient, said MPS further generating second time-tagged MPS data sets, each of said second MPS data sets comprising a collection of three-dimensional position coordinate readings wherein each of the readings is associated with a respective time at which the reading was obtained and which demonstrate the overall motion trajectory of said surgical tool over time.

10. The apparatus according to claim 9, wherein said processor constructs trajectories of said surgical tool within said patient body, according to said second time-tagged MPS data sets, respective of different phases of said respiratory trajectory.

11. The apparatus according to claim 9, wherein said organ is a first organ and said organ timing signal is a first organ timing signal, said surgical tool being inserted in a blood vessel in the patient's body in a vicinity of a second, inspected organ different from said first organ, said processor generating a second organ timing signal from said second time-tagged MPS data sets by detecting and identifying periodic motion frequencies in said second time-tagged MPS data sets, and filtering said periodic motion frequencies from second time-tagged said MPS data sets so as to separate out said periodic motion frequencies corresponding to said second organ timing signal from said overall motion trajectory of said surgical tool.

12. The apparatus according to claim 11 wherein said processor further reconstructs a cardiac trajectory from said second time-tagged MPS data sets and said filtered periodic motion frequencies, said cardiac trajectory representing a mechanical movement of a blood vessel originating from cardiac motion.

13. The apparatus according to claim 12 wherein said processor further detects phase information of said second, inspected organ by identifying a plurality of phases on said reconstructed cardiac trajectory.

14. The apparatus according to claim 13 wherein said first organ is a lung and said second, inspected organ is a heart.

15. The apparatus according to claim 13, further comprising:
   a database coupled with said MPS and with said processor, said database storing at least said first and second MPS data sets; and
   a medical imaging device coupled with said database, said medical imaging device including an image detector, said medical imaging device acquiring a plurality of two-dimensional images of said second, inspected organ via said image detector, said database further storing at least said plurality of two-dimensional images,
   wherein said processor further associates between said acquired two-dimensional images, said first and second MPS data sets, and said cardiac phase information, and constructs trajectories of said surgical tool guided within said blood vessel, respective of different phases of said second, inspected organ.

16. The apparatus according to claim 15, wherein said medical imaging device includes an image acquisition system selected from the group comprising:
   ultrasound;
   intra-vascular ultrasound;
   X-ray;
   C-arm machine;
   fluoroscopy;
   angiography;
   computerized tomography;
   nuclear magnetic resonance;
   positron-emission tomography; and
   single-photon-emission tomography.

17. The apparatus according to claim 13, further comprising a display coupled with said processor, said display presenting a motion picture of said second, inspected organ, said motion picture presenting the trajectory of said surgical tool guided within said blood vessel, respective of different phases of said second, inspected organ.

18. The apparatus according to claim 1, further comprising a database coupled with said MPS and with said processor, said database storing at least said MPS data sets.

19. The apparatus according to claim 18, further comprising a medical imaging device coupled with said database, said medical imaging device including an image detector, said medical imaging device acquiring a plurality of two-dimensional images of said organ via said image detector, said database further storing at least said plurality of two-dimensional images.

20. A method for generating an organ timing signal relating to an organ within a body of a patient, the method comprising:
   determining a three-dimensional position of an electromagnetic sensor configured to be attached to an external area of the patient's body to thereby determine the three-dimensional position of the external area, by processing transmitted electromagnetic signals transmitted by a medical positioning system with detected electromagnetic signals detected by the sensor;
   generating time-tagged MPS data sets comprising a collection of time-tagged three-dimensional position coordinate readings wherein each of the readings is associated with a respective time at which the reading was obtained, the readings demonstrating the overall motion trajectory of the sensor over time;
   detecting and identifying periodic motion frequencies in said time-tagged MPS data sets; and
   filtering said periodic motion frequencies from said MPS data sets so as to separate said periodic motion frequencies corresponding to said organ timing signal from said overall motion trajectory of said sensor.

21. An apparatus for generating an organ timing signal relating to an organ within a body of a patient, said apparatus comprising:
   a medical positioning system (MPS) including an electromagnetic sensor configured to be attached to an invasive surgical tool configured to be inserted into the patient body, said MPS being configured to determine a three-dimensional position of said sensor and thereby said surgical tool by processing transmitted electromagnetic signals transmitted by the MPS with detected electromagnetic signals detected by the sensor, said MPS further generating time-tagged MPS data sets, each of said MPS data sets comprising a collection of three-dimensional position coordinate readings wherein each of the readings is associated with a respective time at which the reading was obtained, said readings demonstrating the overall motion trajectory of said surgical tool over time; and
   a processor coupled with said MPS, generating said organ timing signal from said MPS data sets by detecting and identifying periodic motion frequencies in said time-tagged MPS data sets, and filtering said periodic motion frequencies from said MPS data sets so as to separate out said periodic motion frequencies corresponding to said organ timing signal from said overall motion trajectory of said surgical tool.

* * * * *

UNITED STATES PATENT AND TRADEMARK OFFICE
CERTIFICATE OF CORRECTION

PATENT NO. : 9,956,049 B2
APPLICATION NO. : 15/428497
DATED : May 1, 2018
INVENTOR(S) : Itzhak Shmarak, Gera Strommer and Uzi Eichler It is certified that error appears in the above-identified patent and that said Letters Patent is hereby corrected as shown below:

On the Title Page

Page 2, first column, item (63) under Related U.S. Application Data, after 7,778,688, please delete the following:
", which is a continuation-in-part of application No. 09/949,160, filed on Sep. 7, 2001, now Pat. No. 7,343,195, which is a continuation-in-part of application No. 09/782,528, filed on Feb. 13, 2001, now Pat. No. 7,386,339, which is a continuation-in-part of application No. 09/314,474, filed on May 18, 1999, now Pat. No. 6,233,476"

Signed and Sealed this
Twentieth Day of November, 2018

Andrei Iancu
*Director of the United States Patent and Trademark Office*